US009308208B2

(12) United States Patent
Wensley et al.

(10) Patent No.: US 9,308,208 B2
(45) Date of Patent: ***Apr. 12, 2016

(54) AEROSOL GENERATING METHOD AND DEVICE

(75) Inventors: Martin J. Wensley, Los Gatos, CA (US); Daniel Mufson, Napa, CA (US); Craig C. Hodges, Walnut Creek, CA (US); Peter M. Lloyd, Walnut Creek, CA (US); Daniel D. Rogers, Oakland, CA (US)

(73) Assignee: ALEXZA PHARMACEUTICALS, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/847,584

(22) Filed: Jul. 30, 2010

(65) Prior Publication Data
US 2010/0294268 A1  Nov. 25, 2010

Related U.S. Application Data

(63) Continuation of application No. 10/057,197, filed on Oct. 26, 2001, now Pat. No. 7,766,013.

(60) Provisional application No. 60/296,225, filed on Jun. 5, 2001.

(51) Int. Cl.
| *A61K 9/12* | (2006.01) |
| *A61K 9/14* | (2006.01) |
| *A61M 15/00* | (2006.01) |
| *A61K 31/519* | (2006.01) |
| *A61K 9/00* | (2006.01) |
| *B05B 7/16* | (2006.01) |
| *B05B 17/04* | (2006.01) |
| *A61M 11/02* | (2006.01) |
| *A61K 31/235* | (2006.01) |
| *A61K 31/4468* | (2006.01) |
| *A61M 11/00* | (2006.01) |
| *A61M 16/00* | (2006.01) |

(52) U.S. Cl.
CPC ............... *A61K 31/519* (2013.01); *A61K 9/007* (2013.01); *A61K 9/0073* (2013.01); *A61K 31/235* (2013.01); *A61K 31/4468* (2013.01); *A61M 11/001* (2014.02); *A61M 11/02* (2013.01); *A61M 15/00* (2013.01); *A61M 15/0028* (2013.01); *B05B 7/1686* (2013.01); *B05B 17/04* (2013.01); *A61M 2016/0039* (2013.01); *A61M 2205/3606* (2013.01); *A61M 2205/368* (2013.01); *A61M 2205/3653* (2013.01); *A61M 2205/50* (2013.01)

(58) Field of Classification Search
CPC ... A61K 31/519; A61K 9/007; A61K 9/0073; A61M 15/0028
IPC ... A61K 31/519, 9/007, 9/0073; A61M 15/0028
See application file for complete search history.

(56) References Cited

U.S. PATENT DOCUMENTS

| 1,239,634 A | 9/1917 | Stuart |
| 1,535,486 A | 4/1925 | Lundy |
| 1,803,334 A | 5/1931 | Lehmann |
| 1,864,980 A | 6/1932 | Curran |
| 2,084,299 A | 6/1937 | Borden |
| 2,086,140 A | 7/1937 | Ernst |
| 2,230,753 A | 2/1941 | Klavehn et al. |
| 2,230,754 A | 2/1941 | Klavehn et al. |
| 2,243,669 A | 5/1941 | Clyne |
| 2,309,846 A | 2/1943 | Holm |
| 2,469,656 A | 5/1949 | Lienert |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |
| 2,902,484 A | 9/1959 | Horclois |
| 3,043,977 A | 7/1962 | Morowitz |
| 3,080,624 A | 3/1963 | Webber, III |
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,282,729 A | 11/1966 | Richardson et al. |
| 3,296,249 A | 1/1967 | Bell |
| 3,299,185 A | 1/1967 | Oda et al. |
| 3,371,085 A | 2/1968 | Reeder et al. |
| 3,393,197 A | 7/1968 | Pachter |

(Continued)

FOREIGN PATENT DOCUMENTS

| CA | 2152684 | 1/1996 |
| CN | 1082365 | 2/1994 |
| CN | 1176075 | 3/1998 |
| DE | 198 54 007 | 5/2000 |
| EP | 0 039 369 | 11/1981 |
| EP | 0 274 431 | 7/1988 |
| EP | 0 277 519 | 8/1988 |
| EP | 0 358 114 | 3/1990 |
| EP | 0 430 559 | 6/1991 |
| EP | 0 492 485 | 7/1992 |

(Continued)

OTHER PUBLICATIONS

U.S. Appl. No. 12/628,949, filed Dec. 1, 2009, Zaffaroni et al.

(Continued)

*Primary Examiner* — Mina Haghighatian

(74) *Attorney, Agent, or Firm* — Swanson & Bratschun, L.L.C.

(57) ABSTRACT

A method and device are provided to generate an aerosol having a desired particle sizes, i.e., from molecular to about 10 microns, which can be used to effectively deliver a physiologically active compound to organs and tissues such as the lung, eye, mucosa and skin. The aerosol is formed through vaporization of the compound while mixing the resulting vapor with a gas, in a ratio, to form the desired particle size when a stable concentration of particles in the gas is reached.

32 Claims, 14 Drawing Sheets

(56) References Cited

U.S. PATENT DOCUMENTS

| | | |
|---|---|---|
| 3,433,791 A | 3/1969 | Bentley et al. |
| 3,560,607 A | 2/1971 | Hartley et al. |
| 3,701,782 A | 10/1972 | Hester |
| 3,749,547 A | 7/1973 | Gregory et al. |
| 3,763,347 A | 10/1973 | Whitaker et al. |
| 3,773,995 A | 11/1973 | Pachter et al. |
| 3,831,606 A | 8/1974 | Damani |
| 3,847,650 A | 11/1974 | Gregory et al. |
| 3,864,326 A | 2/1975 | Babington |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick et al. |
| 4,020,379 A | 4/1977 | Manning |
| 4,045,156 A | 8/1977 | Chu et al. |
| 4,079,742 A | 3/1978 | Rainer et al. |
| 4,104,210 A | 8/1978 | Coran et al. |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,198,200 A | 4/1980 | Fonda et al. |
| RE30,285 E | 5/1980 | Babington |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,346,059 A | 8/1982 | Spector |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,523,589 A | 6/1985 | Krauser |
| 4,556,539 A | 12/1985 | Spector |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III et al. |
| 4,683,231 A | 7/1987 | Glassman |
| 4,693,868 A | 9/1987 | Katsuda et al. |
| 4,708,151 A | 11/1987 | Shelar |
| 4,714,082 A | 12/1987 | Banerjee et al. |
| 4,722,334 A | 2/1988 | Blackmer et al. |
| 4,734,560 A | 3/1988 | Bowen |
| 4,735,217 A | 4/1988 | Gerth et al. |
| 4,735,358 A | 4/1988 | Morita et al. |
| 4,753,758 A | 6/1988 | Miller |
| 4,755,508 A | 7/1988 | Bock et al. |
| 4,756,318 A | 7/1988 | Clearman et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,852,561 A | 8/1989 | Sperry |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,892,109 A | 1/1990 | Strubel |
| 4,895,719 A | 1/1990 | Radhakrishnan et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A | 5/1990 | Brooks et al. |
| 4,924,883 A | 5/1990 | Perfetti et al. |
| 4,928,714 A | 5/1990 | Shannon |
| 4,935,624 A | 6/1990 | Henion et al. |
| 4,941,483 A | 7/1990 | Ridings et al. |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz et al. |
| 4,968,885 A | 11/1990 | Willoughby |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman et al. |
| 5,020,548 A | 6/1991 | Farrier et al. |
| 5,027,836 A | 7/1991 | Shannon et al. |
| 5,033,483 A | 7/1991 | Clearman et al. |
| 5,038,769 A | 8/1991 | Krauser |
| 5,042,509 A | 8/1991 | Banerjee et al. |
| 5,049,389 A | 9/1991 | Radhakrishnan |
| 5,060,666 A | 10/1991 | Clearman et al. |
| 5,060,667 A | 10/1991 | Strubel |
| 5,060,671 A | 10/1991 | Counts et al. |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,093,894 A | 3/1992 | Deevi et al. |
| 5,095,921 A | 3/1992 | Losee et al. |
| 5,099,861 A | 3/1992 | Clearman et al. |
| 5,105,831 A | 4/1992 | Banerjee et al. |
| 5,109,180 A | 4/1992 | Boultinghouse et al. |
| 5,112,598 A | 5/1992 | Biesalski |
| 5,118,494 A | 6/1992 | Schultz et al. |
| 5,119,834 A | 6/1992 | Shannon et al. |
| 5,126,123 A | 6/1992 | Johnson |
| 5,133,368 A | 7/1992 | Neumann et al. |
| 5,135,009 A | 8/1992 | Muller et al. |
| 5,137,034 A | 8/1992 | Perfetti et al. |
| 5,144,962 A | 9/1992 | Counts et al. |
| 5,146,915 A | 9/1992 | Montgomery |
| 5,149,538 A | 9/1992 | Granger et al. |
| 5,156,170 A | 10/1992 | Clearman et al. |
| 5,160,664 A | 11/1992 | Liu |
| 5,164,740 A | 11/1992 | Ivri |
| 5,166,202 A | 11/1992 | Schweizer |
| 5,167,242 A | 12/1992 | Turner et al. |
| 5,168,866 A | 12/1992 | Montgomery et al. |
| 5,177,071 A | 1/1993 | Freidinger et al. |
| 5,179,966 A | 1/1993 | Losee et al. |
| 5,186,164 A | 2/1993 | Raghuprasad |
| 5,192,528 A * | 3/1993 | Radhakrishnan et al. ...... 424/45 |
| 5,192,548 A | 3/1993 | Velasquez et al. |
| 5,224,498 A | 7/1993 | Deevi et al. |

(56) References Cited

U.S. PATENT DOCUMENTS

| | | |
|---|---|---|
| 5,226,411 A | 7/1993 | Levine |
| 5,229,120 A | 7/1993 | DeVincent |
| 5,229,382 A | 7/1993 | Chakrabarti et al. |
| 5,240,922 A | 8/1993 | O'Neill |
| 5,249,586 A | 10/1993 | Morgan et al. |
| 5,255,674 A | 10/1993 | Oftedal et al. |
| 5,261,424 A | 11/1993 | Sprinkel, Jr. |
| 5,264,433 A | 11/1993 | Sato et al. |
| 5,269,327 A | 12/1993 | Counts et al. |
| 5,284,133 A | 2/1994 | Burns et al. |
| 5,285,798 A | 2/1994 | Banerjee et al. |
| 5,292,499 A | 3/1994 | Evans et al. |
| 5,322,075 A | 6/1994 | Deevi et al. |
| 5,333,106 A | 7/1994 | Lanpher et al. |
| 5,345,951 A | 9/1994 | Serrano et al. |
| 5,357,984 A | 10/1994 | Farrier et al. |
| 5,363,842 A | 11/1994 | Mishelevich et al. |
| 5,364,838 A | 11/1994 | Rubsamen |
| 5,366,770 A | 11/1994 | Wang |
| 5,372,148 A | 12/1994 | McCafferty et al. |
| 5,376,386 A | 12/1994 | Ganderton et al. |
| 5,388,574 A | 2/1995 | Ingebrethsen |
| 5,391,081 A | 2/1995 | Lampotang et al. |
| 5,399,574 A | 3/1995 | Robertson et al. |
| 5,400,808 A | 3/1995 | Turner et al. |
| 5,400,969 A | 3/1995 | Keene |
| 5,402,517 A | 3/1995 | Gillett et al. |
| 5,408,574 A | 4/1995 | Deevi et al. |
| 5,436,230 A | 7/1995 | Soudant et al. |
| 5,451,408 A | 9/1995 | Mezei et al. |
| 5,455,043 A | 10/1995 | Fischel-Ghodsian |
| 5,456,247 A | 10/1995 | Shilling et al. |
| 5,456,677 A | 10/1995 | Spector |
| 5,457,100 A | 10/1995 | Daniel |
| 5,457,101 A | 10/1995 | Greenwood et al. |
| 5,459,137 A | 10/1995 | Andrasi et al. |
| 5,462,740 A | 10/1995 | Evenstad et al. |
| 5,468,936 A | 11/1995 | Deevi et al. |
| 5,479,948 A | 1/1996 | Counts et al. |
| 5,501,236 A | 3/1996 | Hill et al. |
| 5,505,214 A | 4/1996 | Collins et al. |
| 5,507,277 A | 4/1996 | Rubsamen et al. |
| 5,511,726 A | 4/1996 | Greenspan et al. |
| 5,519,019 A | 5/1996 | Andrasi et al. |
| 5,525,329 A | 6/1996 | Snyder et al. |
| 5,537,507 A | 7/1996 | Mariner et al. |
| 5,538,020 A | 7/1996 | Farrier et al. |
| 5,540,959 A | 7/1996 | Wang |
| 5,543,434 A | 8/1996 | Weg |
| 5,544,646 A | 8/1996 | Lloyd et al. |
| 5,564,442 A | 10/1996 | MacDonald et al. |
| 5,565,148 A | 10/1996 | Pendergrass |
| 5,577,156 A | 11/1996 | Costello |
| 5,584,701 A | 12/1996 | Lampotang et al. |
| 5,586,550 A | 12/1996 | Ivri et al. |
| 5,591,409 A | 1/1997 | Watkins |
| 5,592,934 A | 1/1997 | Thwaites |
| 5,593,792 A | 1/1997 | Farrier et al. |
| 5,605,146 A | 2/1997 | Sarela |
| 5,605,897 A | 2/1997 | Beasley, Jr. et al. |
| 5,607,691 A | 3/1997 | Hale et al. |
| 5,613,504 A | 3/1997 | Collins et al. |
| 5,613,505 A | 3/1997 | Campbell et al. |
| 5,619,984 A | 4/1997 | Hodson et al. |
| 5,622,944 A | 4/1997 | Hale et al. |
| 5,627,178 A | 5/1997 | Chakrabarti et al. |
| 5,649,554 A | 7/1997 | Sprinkel |
| 5,655,523 A | 8/1997 | Hodson et al. |
| 5,656,255 A | 8/1997 | Jones |
| 5,660,166 A | 8/1997 | Lloyd et al. |
| 5,666,977 A | 9/1997 | Higgins et al. |
| 5,690,809 A | 11/1997 | Subramaniam et al. |
| 5,694,919 A | 12/1997 | Rubsamen et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,767,117 A | 6/1998 | Moskowitz et al. |
| 5,769,621 A | 6/1998 | Early et al. |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,855,564 A | 1/1999 | Ruskewicz |
| 5,855,913 A | 1/1999 | Hanes et al. |
| 5,865,185 A | 2/1999 | Collins et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,904,900 A | 5/1999 | Bleuse et al. |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang et al. |
| 5,934,272 A | 8/1999 | Lloyd et al. |
| 5,934,289 A | 8/1999 | Watkins et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda et al. |
| 5,971,951 A | 10/1999 | Ruskewicz |
| 5,985,309 A | 11/1999 | Edwards et al. |
| 5,993,805 A | 11/1999 | Sutton et al. |
| 6,004,516 A | 12/1999 | Rasouli et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,013,050 A | 1/2000 | Bellhouse et al. |
| 6,014,969 A | 1/2000 | Lloyd et al. |
| 6,014,970 A | 1/2000 | Ivri et al. |
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| 6,053,176 A | 4/2000 | Adams et al. |
| RE36,744 E | 6/2000 | Goldberg |
| 6,085,026 A | 7/2000 | Hammons et al. |
| 6,089,857 A | 7/2000 | Matsuura et al. |
| 6,090,212 A | 7/2000 | Mahawili |
| 6,090,403 A | 7/2000 | Block et al. |
| 6,095,134 A | 8/2000 | Sievers et al. |
| 6,095,153 A | 8/2000 | Kessler et al. |
| 6,098,620 A | 8/2000 | Lloyd et al. |
| 6,102,036 A | 8/2000 | Slutsky et al. |
| 6,113,795 A | 9/2000 | Subramaniam et al. |

(56) References Cited

U.S. PATENT DOCUMENTS

| | | |
|---|---|---|
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,570 A | 10/2000 | Schuster et al. |
| 6,133,327 A | 10/2000 | Kimura et al. |
| 6,135,369 A | 10/2000 | Prendergast et al. |
| 6,136,295 A | 10/2000 | Edwards et al. |
| 6,138,683 A | 10/2000 | Hersh et al. |
| 6,140,323 A | 10/2000 | Ellinwood, Jr. et al. |
| 6,143,277 A | 11/2000 | Ashurst et al. |
| 6,143,746 A | 11/2000 | Daugan et al. |
| 6,149,892 A | 11/2000 | Britto |
| 6,155,268 A | 12/2000 | Takeuchi |
| 6,158,431 A | 12/2000 | Poole |
| 6,167,880 B1 | 1/2001 | Gonda et al. |
| 6,178,969 B1 | 1/2001 | St. Charles |
| 6,234,167 B1 | 5/2001 | Cox et al. |
| 6,241,969 B1 | 6/2001 | Saidi et al. |
| 6,250,301 B1 | 6/2001 | Pate |
| 6,255,334 B1 | 7/2001 | Sands |
| 6,263,872 B1 | 7/2001 | Schuster et al. |
| 6,264,922 B1 | 7/2001 | Wood et al. |
| 6,284,287 B1 | 9/2001 | Sarlikiotis et al. |
| 6,299,900 B1 | 10/2001 | Reed et al. |
| 6,300,710 B1 | 10/2001 | Nakamori |
| 6,306,431 B1 | 10/2001 | Zhang et al. |
| 6,309,668 B1 | 10/2001 | Bastin et al. |
| 6,309,986 B1 | 10/2001 | Flashinski et al. |
| 6,313,176 B1 | 11/2001 | Ellinwood, Jr. et al. |
| 6,325,475 B1 | 12/2001 | Hayes et al. |
| 6,376,550 B1 | 4/2002 | Raber et al. |
| 6,390,453 B1 | 5/2002 | Frederickson et al. |
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,461,591 B1 | 10/2002 | Keller et al. |
| 6,491,233 B2 | 12/2002 | Nichols |
| 6,501,052 B2 | 12/2002 | Cox et al. |
| 6,506,762 B1 | 1/2003 | Horvath et al. |
| 6,514,482 B1 | 2/2003 | Bartus et al. |
| 6,516,796 B1 | 2/2003 | Cox et al. |
| 6,557,552 B1 | 5/2003 | Cox et al. |
| 6,561,186 B2 | 5/2003 | Casper et al. |
| 6,568,390 B2 | 5/2003 | Nichols et al. |
| 6,591,839 B2 | 7/2003 | Meyer et al. |
| 6,632,047 B2 | 10/2003 | Vinegar et al. |
| 6,648,950 B2 | 11/2003 | Lee et al. |
| 6,671,945 B2 | 1/2004 | Gerber et al. |
| 6,680,668 B2 | 1/2004 | Gerber et al. |
| 6,681,769 B2 | 1/2004 | Sprinkel et al. |
| 6,681,998 B2 | 1/2004 | Sharpe et al. |
| 6,682,716 B2 | 1/2004 | Hodges et al. |
| 6,688,313 B2 | 2/2004 | Wrenn et al. |
| 6,694,975 B2 | 2/2004 | Schuster et al. |
| 6,701,921 B2 | 3/2004 | Sprinkel et al. |
| 6,701,922 B2 | 3/2004 | Hindle et al. |
| 6,715,487 B2 | 4/2004 | Nichols et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,728,478 B2 | 4/2004 | Cox et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,772,757 B2 | 8/2004 | Sprinkel, Jr. et al. |
| 6,776,978 B2 | 8/2004 | Zaffaroni et al. |
| 6,779,520 B2 | 8/2004 | Genova et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Ron et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |

(56) References Cited

U.S. PATENT DOCUMENTS

| | | | |
|---|---|---|---|
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 2001/0020147 A1 | 9/2001 | Staniforth et al. |
| 2001/0042546 A1 | 11/2001 | Umeda et al. |
| 2002/0031480 A1 | 3/2002 | Peart et al. |
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0078955 A1 | 6/2002 | Nichols et al. |
| 2002/0086852 A1 | 7/2002 | Cantor |
| 2002/0097139 A1 | 7/2002 | Gerber et al. |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0032638 A1 | 2/2003 | Kim et al. |
| 2003/0033055 A1 | 2/2003 | McRae et al. |
| 2003/0049025 A1 | 3/2003 | Neumann et al. |
| 2003/0051728 A1 | 3/2003 | Lloyd et al. |
| 2003/0106551 A1 | 6/2003 | Sprinkel et al. |
| 2003/0118512 A1 | 6/2003 | Shen |
| 2003/0121906 A1 | 7/2003 | Abbott et al. |
| 2003/0131843 A1 | 7/2003 | Lu |
| 2003/0132219 A1 | 7/2003 | Cox et al. |
| 2003/0138508 A1 | 7/2003 | Novack et al. |
| 2003/0156829 A1 | 8/2003 | Cox et al. |
| 2004/0009128 A1 | 1/2004 | Rabinowitz et al. |
| 2004/0016427 A1 | 1/2004 | Byron et al. |
| 2004/0035409 A1 | 2/2004 | Harwig et al. |
| 2004/0055504 A1 | 3/2004 | Lee et al. |
| 2004/0081624 A1 | 4/2004 | Nguyen et al. |
| 2004/0096402 A1 | 5/2004 | Hodges et al. |
| 2004/0099266 A1 | 5/2004 | Cross et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2006/0032496 A1 | 2/2006 | Hale et al. |
| 2006/0120962 A1 | 6/2006 | Rabinowitz et al. |
| 2006/0193788 A1 | 8/2006 | Hale et al. |
| 2006/0257329 A1 | 11/2006 | Rabinowitz et al. |
| 2007/0122353 A1 | 5/2007 | Hale et al. |
| 2007/0140982 A1 | 6/2007 | Every et al. |
| 2007/0286816 A1 | 12/2007 | Hale et al. |
| 2008/0038363 A1 | 2/2008 | Zaffaroni et al. |
| 2008/0110872 A1 | 5/2008 | Hale et al. |
| 2008/0175796 A1 | 7/2008 | Rabinowitz et al. |
| 2008/0216828 A1 | 9/2008 | Wensley |
| 2008/0299048 A1 | 12/2008 | Hale et al. |
| 2008/0306285 A1 | 12/2008 | Hale et al. |
| 2008/0311176 A1 | 12/2008 | Hale et al. |
| 2009/0062254 A1 | 3/2009 | Hale et al. |
| 2009/0071477 A1 | 3/2009 | Hale et al. |
| 2009/0180968 A1 | 7/2009 | Hale et al. |
| 2009/0229600 A1 | 9/2009 | Hale et al. |
| 2009/0235926 A1 | 9/2009 | Cross |
| 2009/0246147 A1 | 10/2009 | Rabinowitz et al. |
| 2009/0258075 A1 | 10/2009 | Hale et al. |
| 2009/0301363 A1 | 12/2009 | Damani et al. |
| 2010/0006092 A1 | 1/2010 | Hale et al. |
| 2010/0055048 A1 | 3/2010 | Hale et al. |
| 2010/0065052 A1 | 3/2010 | Sharma et al. |
| 2010/0068154 A1 | 3/2010 | Sharma et al. |
| 2010/0068155 A1 | 3/2010 | Lei et al. |
| 2010/0294268 A1 | 11/2010 | Wensley et al. |
| 2010/0300433 A1 | 12/2010 | Sharma et al. |
| 2011/0240013 A1* | 10/2011 | Hale et al. ............... 128/200.14 |
| 2011/0245493 A1* | 10/2011 | Rabinowitz et al. ........ 540/592 |

FOREIGN PATENT DOCUMENTS

| | | |
|---|---|---|
| EP | 0 606 486 | 7/1994 |
| EP | 0 734 719 | 2/1996 |
| EP | 0 967 214 | 12/1999 |
| EP | 1 080 720 | 3/2001 |
| EP | 1 177 793 | 2/2002 |
| EP | 0 808 635 B1 | 7/2003 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| HU | 200105 B | 10/1988 |
| HU | 219392 B | 6/1993 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/36574 | 10/1997 |
| WO | WO 97/40819 | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/16419 | 4/1999 |
| WO | WO 99/24433 | 5/1999 |

(56) References Cited

FOREIGN PATENT DOCUMENTS

| | | |
|---|---|---|
| WO | WO 99/37347 | 7/1999 |
| WO | WO 99/37625 | 7/1999 |
| WO | WO 99/44664 | 9/1999 |
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/43801 | 6/2001 |
| WO | WO 01/95903 | 12/2001 |
| WO | WO 02/00198 | 1/2002 |
| WO | WO 02/24158 | 3/2002 |
| WO | WO 02/051466 | 7/2002 |
| WO | WO 02/056866 | 7/2002 |
| WO | WO 02/094234 | 11/2002 |
| WO | WO 02/098389 | 12/2002 |
| WO | WO 03/037412 | 5/2003 |

OTHER PUBLICATIONS

U.S. Appl. No. 13/078,600, filed Hodges et al., Apr. 1, 2011.
U.S. Appl. No. 13/078,606, filed Hale et al., Apr. 1, 2011.
U.S. Appl. No. 13/078,654, filed Cross et al., Apr. 1, 2011.
U.S. Appl. No. 13/078,668, filed Bennett et al., Apr. 1, 2011.
U.S. Appl. No. 13/078,525, filed Rabinowitz et al., Apr. 1, 2011.
U.S. Appl. No. 13/078,519, filed Hale et al., Apr. 1, 2011.
U.S. Appl. No. 13/078,516, filed Hale et al., Apr. 1, 2011.
Office Action mailed Dec. 4, 2003 with respect to U.S. Appl. No. 10/057,198.
Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Aug. 13, 2003 with respect to U.S. Appl. No. 10/153,313.
Office Action mailed Mar. 8, 2005 with respect to U.S. Appl. No. 10/718,982.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER, pp. 1-110.
Bennett, R. L. et al. (1981). "Patient-Controlled Analgesia: A New Concept of Postoperative Pain Relief," Annual Surg. 195(6):700-705.
Benowitz (1994). "Individual Differences in Nicotine Kinetics and Metabolism in Humans," NIDA Research Monography, 2 pages.
BP: Chemicals Products-Barrier Resins (1999). located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," Journal of Pharmaceutical Sciences. 89(6):724-731.
Campbell, Fiona A. et al. (2001) "Are cannabinoids an effective and safe treatment option in the management of pain? A qualitative systemic review," BMJ, 323 pp. 1-6.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral DELTA 9—tetrahydrocannabinol: Dose response analysis and receptor identification" Journal of Pharmacolgy and Experimental Therapeutics vol. 289 (2): 859-867.
Clark, A. and Byron, P. (1986). "Dependence of Pulmonary Absorption Kinetics on Aerosol Particle Size," Z. Erkrank. 166:13-24.
Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422.
Darquenne, C. et al. (1997). "Aerosol Dispersion in Human Lung: Comparison Between Numerical Simulations and Experiments for Bolus Tests," American Physiological Society. 966-974.
Database Biosis "Online!" Biosciences Information Service, Philadelphia, PA 1979, Knight, V. et al., "Amantadine aerosol in humans", database accession No. PREV 198069035552 abstract, & Antimicrobial Agents and Chemotherapy 16(5):572-578.
Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; AN 1989-297792 AP002230849 & JP 01 221313 (Nippon Create 1(K), Sep. 4, 1989, abstract.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Drugs Approved by the FDA—Drug Name: Nicotrol Inhaler (2000) located at <http://www.centerwatch.com/patient/drugs/dru202.html> (Visited on Aug. 2, 2001), 2 pages.

(56) References Cited

OTHER PUBLICATIONS

Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.

Finlay, W. H. (2001). "The Mechanics of Inhaled Pharmaceutical Aerosols", Academic Press: San Diego Formula 2.39. pp. 3-14 (Table of Contents). pp. v-viii.

Gonda, I. (1991). "Particle Deposition in the Human Respiratory Tract," Chapter 176, The Lung: Scientific Foundations. Crystal R.G. and West, J.B. (eds.), Raven Publishers, New York. pp. 2289-2294.

Graves, D. A. et al. (1983). "Patient-Controlled Analgesia" Annals of Internal Medicine. 99:360-366.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 μm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.

James, A.C. et al., (1991). "The Respiratory Tract Deposition Model Proposed by the ICRP Task Group," Radiation Protection Dosimetry, 38(1/3):159-165.

Kim, M. H. and Patel, D.V. (1994). "'BOP' As a Reagent for Mild and Efficient Preparation of Esters," Tet. Letters 35:5603-5606.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. (Mar. 2000). ACS Conference—San Francisco—Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Poochikian, G. and Bertha, C.M. (2000). "Inhalation Drug Product Excipient Controls: Significance and Pitfalls," Resp. Drug Deliv. VII: 109-115.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

Vapotronics, Inc. (1998) located at http://www.vapotronics.com.au/banner.htm., 11 pages, (visited on Jun. 5, 2000).

Vaughan, N.P. (1990). "The Generation of Monodisperse Fibres of Caffeine" J. Aerosol Sci. 21(3): 453-462.

Ward, M. E. MD, et al. (Dec. 1997). "Morphine Pharmacokinetics after Pulmonary Administration from a Novel Aerosol Delivery System," Clinical Pharmacology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

* cited by examiner

Number Concentration vs Time for Number Concentration to Halve

Coagulation Coefficient vs. Particle Size

Vapor Pressure vs Temperature

Blood Levels vs Time; IV and Inhaled Fentanyl

Fig. 29

Ratio of Vaporized Compound to Volume of Mixing Gas vs. Particle Diameter

AEROSOL GENERATING METHOD AND DEVICE

This application is a continuation of U.S. application Ser. No. 10/057,197, filed Oct. 26, 2001, entitled "Aerosol Generating Method and Device". U.S. application Ser. No. 10/057,197 claims the benefit of prior U.S. provisional application Ser. No. 60/296,225 filed Jun. 5, 2001. The above disclosures are hereby incorporated by reference in their entirety. Any disclaimer that may have occurred during the prosecution of the above-referenced applications is hereby expressly rescinded, and reconsideration of all relevant art is respectfully requested.

FIELD OF THE INVENTION

This invention relates to a method and a device for volatilizing a physiologically active compound and administering the volatilized compound in the form of an aerosol to a patient.

BACKGROUND OF THE INVENTION

An aerosol is defined as an assembly of liquid or solid particles suspended in a gaseous medium. (See Aerosol Measurement, Willeke and Baron, Wiley-Interscience 1993.) It is known that aerosols of appropriate particle size, can be used to deliver drugs to organs and tissues such as the lung and mucosa. (See Gonda, I., "Particle Deposition in the Human Respiratory Tract," *The Lung: Scientific Foundations, 2nd* ed., Crystal, West, et al. editors, Lippincott-Raven Publishers, 1997).

A problem in generating an aerosol is maintaining the purity of a compound being administered into the lung, as an aerosol. This is a critical issue that must be addressed before inhalation delivery of a compound to humans will be acceptable to regulatory agencies, physicians and patients. Any compound administered to humans must meet strict purity requirements regulated by government agencies and industry. For example, the United States Food and Drug Administration mandates purity requirements for pharmaceutical materials sold in the United States to protect the health of consumers of those products. Purity requirements are often material specific. Maximum impurity or degradant levels are specified at the time of manufacture of compounds as well as at the time of their consumption or administration. Any aerosolization device or process that will be utilized for pharmaceutical applications, therefore, must deliver materials meeting purity requirements. Mechanisms of chemical degradation that might occur during vaporization and aerosolization, the processes relevant to this invention, are discussed below.

Currently approved products for inhalation administration of physiologically acting compounds can be divided into several categories: dry powder inhalers, nebulizers, and pressurized metered dose inhalers. The desired particle size of these methods and devices usually are in the fine aerosol region (1-3 micron) and not in the ultra fine region (10-100 nm). A large percentage of these devices fall short of the type of particle size control desirable for reproducible and efficient delivery of compounds to the lung. Additionally current devices focus on the fine aerosol region because to date a practical device that can reproducibly generate an ultra fine aerosol has not been commercially available for drug delivery to the lung.

There are many types of dry powder inhalers (DPI's) on the market with some common problems. The first problem is the manufacturing of the dry powder. For a dry powder inhalation system it is necessary to mill the drug until it falls into the desirable particle range. Some mills used for micronization are known to produce heat, which can cause degradation of the drug, and tend to shed metallic particles as contaminants. Following milling it is often necessary to mix the drug with a carrier to impart flowability. The micronized drug and the drug-excipient mix must be maintained in a dry atmosphere lest moisture cause agglomeration of the drug into larger particles. Additionally it is well known that many dry powders grow as they are delivered to the patient's airways due to the high levels of moisture present in the lung. Thus, this approach requires scrupulous attention during milling, blending, powder flow, filling and even administration to assure that the patient receives the proper particle size distribution.

Nebulizers generate an aerosol from a liquid, some by breakup of a liquid jet and some by ultrasonic vibration of the liquid with or without a nozzle. All liquid aerosol devices must overcome the problems associated with formulation of the compound into a stable liquid state. Liquid formulations must be prepared and stored under aseptic or sterile conditions since they can harbor microorganisms. This necessitates the use of preservatives or unit dose packaging. Additionally solvents, detergents and other agents are used to stabilize the drug formulation. The FDA is increasingly concerned about airway hypersensitivity from these agents.

Pressurized metered dose inhalers, or pMDI's, are an additional class of aerosol dispensing devices. PMDI's package the compound in a canister under pressure with a solvent and propellant mixture, usually chlorofluorocarbons (CFC's, which are being phased out due to environmental concerns), or hydroflouroalkanes (HFA's). Upon being dispensed a jet of the mixture is ejected through a valve and nozzle and the propellant "flashes off" leaving an aerosol of the compound. With pMDI's particle size is hard to control and has poor reproducibility leading to uneven and unpredictable bioavailability. pMDIs are inefficient because a portion of the dose is lost on the walls of the actuator, and due to the high speed ejection of the aerosol from the nozzle, much of the drug impacts ballistically on the tongue, mouth and throat and never gets to the lung.

Another method suggested in the prior art to generate aerosols is to volatilize the drug and administer the vapor to a patient. (See Rosen, PCT Publication No. 94/09842, published May 11, 1994.) However, the teaching of Rosen is not a viable solution to the problem because it yields (1) a large quantity of degradation products, and (2) too much variability in particle size distribution (PSD) to insure reproducible and predictable bioavailability.

Predicting the reactions that result in a compound's degradation, and anticipating the energies necessary to activate those reactions are typically very difficult. Reactions may involve only the parent compound or may involve other chemicals such as oxygen in air and materials in the surfaces to which the compound may be exposed. Reactions may be single step or multiple steps, leading to the potential of many degradation products. Activation energies of these reactions depend on molecular structures, energy transfer mechanisms, transitory configurations of the reacting molecular complexes, and the effects of neighboring molecules. Frequently, on the practical macroscopic scale, a drug dose may suffer from many degradation reactions in progress at the same time. Because of this complex potential for degradation, drug substances are often stored at or below room temperature. International health authorities recommend that the stability of a drug be evaluated under exaggerated (stress) conditions to determine the mechanism of degradation and the degradant structures. (See Guidance for Industry: Stability testing of drug substances and products; FDA CDER May 27, 1998). For these tests, 50° C. is recognized as a stress temperature.

The present invention overcomes the foregoing disadvantages and problems, making it possible to produce pure aerosols of degradable compounds wherein the particle size is stable and selectable.

SUMMARY OF THE INVENTION

Embodiments of the present invention are directed to a method and a device for generating and delivering an aerosol formed through vaporization of a compound with real or potential physiological activity.

A physiologically active compound with real or potential physiological activity is defined here as a chemical compound or mixture of compounds that alters affects, treats, cures, prevents or diagnoses a disease after it is administered to the mammalian body. The compound with real or potential physiological activity will be referred to hereafter as the compound or as the drug. Examples would include medicinal drugs, or "pro-drugs" (substances converted into drugs within the body), that would be administered for the treatment, cure, or diagnosis of diseases.

The method of the present invention for generating an aerosol comprises the steps:

(a) heating the physiologically active compound to vaporize at least a portion of the compound, and (b) mixing the resulting vapor with a gas, in a ratio, to form a desired particle size when a stable concentration of particles in the gas is reached.

A desired particle size is typically from molecular to about 10 microns in diameter. Aerosols having "ultra fine" (0.01 to 0.1 micron) and "fine" (1 to 3 micron) particle sizes are known to provide efficient and effective systemic delivery through the lung. Current literature suggests that the middle size range of particles, between ultra fine and fine, i.e., between 0.1 and 1 micron in size, are too small to settle onto the lung wall and too massive to diffuse to the wall in a timely manner. Thus, a significant number of such particles are removed from the lung by exhalation, and thus are not involved in treating disease (see Gonda).

The above method creates a mixture of vapor and gas in a ratio and under conditions suitable to generate an aerosol of particles of a desired size range for effective and efficient administration to a patient. For the purposes of controlling particle size the terms "air", "mixing gas", "dilution gas" and "carrier gas" are interchangeable.

Various alternatives to generate the desired aerosol in accordance with the method of the present invention are summarized here:

1. Heating to vaporize the compound while simultaneously mixing it with a gas in a ratio to permit condensation and aggregation into particles of the desired size.

2. Heating to vaporize the compound to create a pure vapor to permit condensation and aggregation into particles of the desired size.

3. Heating to vaporize the compound to create a pure vapor, followed by introduction of the vapor to a gas in a ratio to permit condensation and aggregation into particles of the desired size.

4. Mixing the aerosols created by the means in 1, 2, or 3 above with additional gas to arrest aggregation and stabilize particle size.

BRIEF DESCRIPTION OF THE DRAWINGS

Further features and advantages will become apparent from the following description of various embodiments of the invention, as illustrated in the accompanying drawings in which:

FIG. 29 is a plot of the theoretical size (diameter) of an aerosol as a function of the ratio of the vaporized compound to the volume of the mixing gas.

DETAILED DESCRIPTION

In the method and device of the present invention, compounds with real or potential physiological activity can be volatilized without medicinally significant degradation and the resulting vapors controlled to form aerosols with particle sizes useful for the administration of the compound to a patient.

In the preferred embodiments of the present invention, compounds are volatilized into vapors avoiding medicinally-significant degradation and thus maintaining acceptable compound purity by the steps of (1) heating the physiologically active compound to a temperature for a limited time and (2) under the conditions of step (1), simultaneously passing a gas across the surface of the compound.

Figure 25:
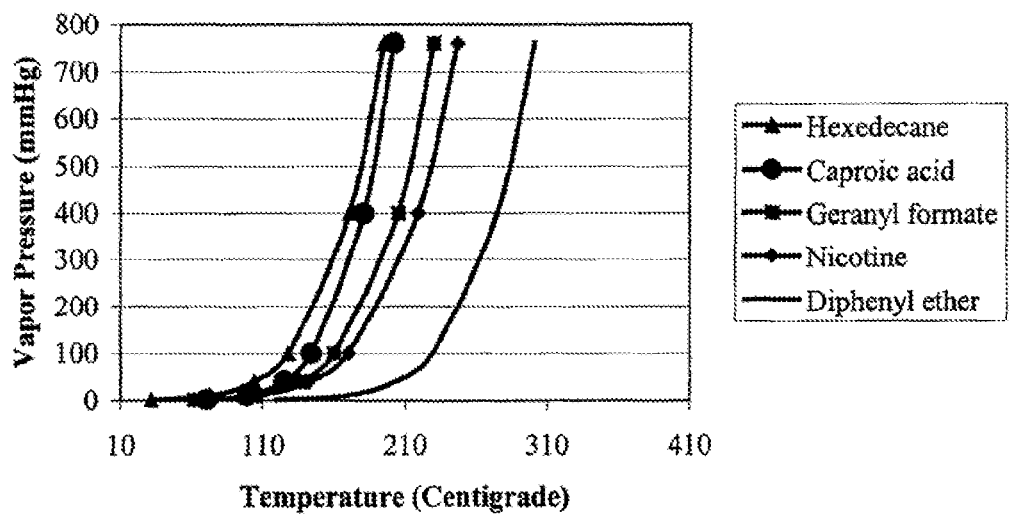
FIG. 25 is a plot of vapor pressure of various compounds, e.g., diphenyl ether, hexadecane, geranyl formate and caproic acid, versus temperature.

As described previously in the BACKGROUND OF THE INVENTION section, it is often difficult to predict the susceptibility to, and the mechanisms and conditions of chemical degradation for a compound of pharmaceutical potential. As a rule, therefore, such compounds are typically protected from temperatures above room temperature. However, vaporization is slow at low temperatures as evidenced by the rapid decline in the equilibrium vapor pressure as a compound's temperature decreases below its boiling point. The plot in FIG. 25 of the vapor pressures for a number of compounds shows that a small decrease in temperature below the boiling point results in a large drop in vapor pressure. At temperatures roughly 200° C. below the compound's boiling point, the vapor pressure is between 25 and 50 mm of Hg. A vapor pressure of 50 mm Hg implies that the ratio of the volumes of the compound vapor to the atmospheric gases above the liquid compound is 50/760.

In view of the foregoing, vaporization has not previously been viewed as a reasonable mechanism for the delivery of most pharmaceutical compounds. In fact, it is common practice to create a form of a medicinal compound that is chemically and physically stable at room temperature to deter vaporization. This can be accomplished by creating a salt, which has a higher melting point and boiling point than the parent molecule.

The present invention, however, makes vaporization a practical delivery method in part, by utilizing a flow of gas across the surface of the compound, to create a dynamic situation in which a compound's vapor molecules are swept away from its surface, driving the chemical equilibrium process towards further vaporization. For many compounds, this method creates a practical rate of vaporization with only moderate heating. Thus, 1 mg of nicotine, (boiling point of 247° C./745 mm), for example, was observed to vaporize around 130° C. in less than 2 seconds with a laboratory device of the present invention described in detail in the EXAMPLES below. Similarly, fentanyl, which decomposes rapidly at 300° C. before reaching its boiling point, was vaporized in quantities up to 2 mg at temperatures around 190° C. Vaporization can therefore be accomplished with the embodiments of this invention at practical rates, i.e., in the range of about 0.5 to about 2 mg/second, and at temperatures much below the compounds' boiling points. The ability to vaporize at these reduced temperatures provides a means to lower rates of degradation reactions in many compounds.

However, even these lower temperatures noted above could lead to significant decomposition for some compounds, so the ability of the present invention to also limit the time during which the compound is exposed to an elevated temperature is also critical. Limiting the exposure time of a compound to temperature is accomplished by rapid heating of a thin film of a deposited compound followed by immediate cooling of the compound vapors as they enter a carrier gas stream. In the preferred embodiments, the compound is moved quickly through a heating/mixing zone to facilitate a rapid temperature rise on the order of 2,000° C./second. Compounds thus reach vaporization temperatures in ten's of milliseconds. Under these conditions, compound molecules quickly escape as vapors from thin layers of deposited compound, and move into a cool carrier gas stream that flows across the surface of the compound. The vapor molecules, thus quickly created, lose their thermal energy when they collide with molecules of the cooler carrier gas.

The method of the present invention, which uses rapid heating to reach vaporization temperatures of compounds, and after vaporization, rapid cooling of the vapor, has been shown to be significant in reducing decomposition, one of the obstacles to generating the desired aerosol. Lipophilic substance #87, for example, decomposed by more than 90% when heated at 425° C. for 5 minutes, but only 20% when the temperature was lowered to 350° C. Decomposition was lowered further to about 12% when the time was decreased to 30 seconds, and to less than 2% when the time was decreased to 10-50 milliseconds. Similarly, 100% of a fentanyl sample decomposed when heated to 200° C. for 30 seconds, but decreased to 15-30% decomposition when fentanyl was heated to 280° C. for 10 milliseconds. When fentanyl was vaporized using the laboratory device, which minimized the vaporization temperature and limited the exposure time to that temperature, no medicinally significant decomposition (<0.1%) was observed.

After a compound has been vaporized, the method of this invention also overcomes the second obstacle to generating the desired aerosol by controlling the generated compound vapors so that an aerosol is formed that (1) is comprised of particles within a desired size range and (2) these particles are sufficiently stable so they will retain their sizes within that range during the time necessary to administer the aerosol to a patient. Particle size is usually expressed as the equivalent diameter of a spherical particle with the same physical behavior. The range of particle sizes in an aerosol is most often described by its mass median diameter (MMD) or mass median aerodynamic diameter (MMAD), and its geometric standard deviation (GSD). As the size of the particles is changed, the site of deposition within the lung can be changed. This can allow targeting of the site of deposition of the compound in the lung and airways.

The method of the present invention forms an aerosol with particles of a desired size range and stability by applying the principle that particle growth can be predicted from the number concentration of the particles in a given volume. In high concentrations, particles frequently collide and adhere to each other. Such a collision and adhesion event (aggregation) creates one particle from two smaller ones. In a population of particles in an aerosol, these events lead to an increase in mean particle size and a decrease in number concentration. The frequency of collisions among particles then decreases, since there are fewer particles available and because the remaining larger particles move more slowly. As a consequence, the rate of particle size growth slows. (See "Aerosol Technology" W. C. Hinds, second edition 1999, Wiley, New York) The term "stable particle size" can be applied in a practical sense when particle size growth has slowed sufficiently to ensure the purpose of the application. For the purposes of drug delivery by inhalation, a stable particle would be one that exists in the ultra fine or fine size range for the 1 to 3 seconds required for a typical inhalation.

In accordance with the present invention, a particle of the ultra fine or fine size range is produced that is stable for several seconds. Also in accordance with the present invention, a predetermined amount of compound in its vapor-state can be mixed into a predetermined volume of a carrier gas in a ratio to give particles of a desired size as the number concentration of the aerosol itself becomes stable. As detailed below, a stable number concentration is approximately $10^9$ particles/cc.

The method of the present invention forms the aerosol with particles of a desired size range and stability by controlling the rate of vaporization, the rate of introduction of a carrier gas, and the mixing of the vapors and the carrier gas, thereby manipulating the parameters that govern the physical processes of a compound's condensation and particle aggregation.

Controlling the ratio of the vaporized compound to the volume of mixing air can be done by a number of methods including: (a) measuring the quantity and regulating the flow rate of the mixing air; and/or (b) regulating the vaporization rate of the compound, e.g. changing the energy transferred to the compound during the heating process or changing the amount of compound introduced into a heating region. As the size of the particles is changed, the site of deposition within the lung can be changed. This can allow targeting of the site of deposition of the compound in the lung and airways.

A desired particle size is achieved by mixing a compound in its vapor-state into a volume of a carrier gas, in a ratio such that when the number concentration of the mixture reaches approximately $10^9$ particles/ml, a "stable" particle size is present. The amount of compound and the volume of gas are each predetermined to achieve this ratio.

Figure 23:
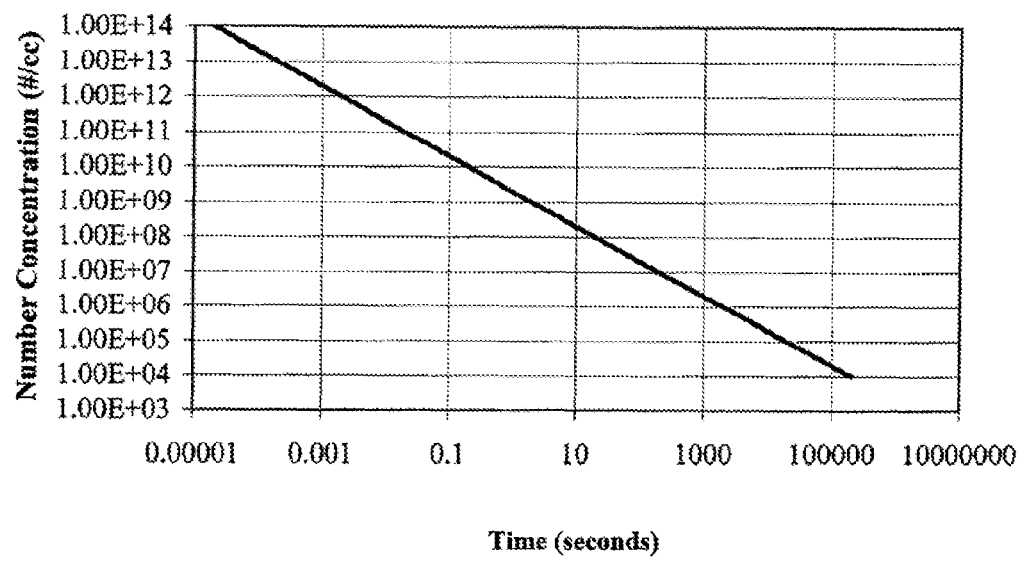
FIG. 23 is a plot of the rate of aggregation of smaller particles into larger ones.

FIG. 23 shows the time in seconds it takes for the number concentration of an aerosol to aggregate to half of its original value as a function of the particle concentration. It is a plot of theoretical data calculated from a mathematical model (See Hinds). For example, a 1.0 mg vaporized dose of a compound with a molecular weight of 200 that is mixed into 1 liter of air will have approximately $3 \times 10^{18}$ molecules (particles) in the liter. This results in a number concentration of $3 \times 10^{15}$/cc. Extrapolating from FIG. 23, one can see that the time required for the number of particles to halve in this example is less than 10 microseconds. This demonstrates that to insure uniform mixing of the vaporized compound, the mixing must happen in a very short time. Even if the compound is allowed to aggregate in size (for example to 12 nm in diameter), the number concentration is still $1 \times 10^{12}$ particles/cc, and the time required for the number of particles to halve is still about 1 millisecond. FIG. 23 also shows that when the number concentration of the mixture reaches approximately $10^9$ particles/cc, the particle sized will be "stable" for the purpose of drug delivery by inhalation.

Figure 24:
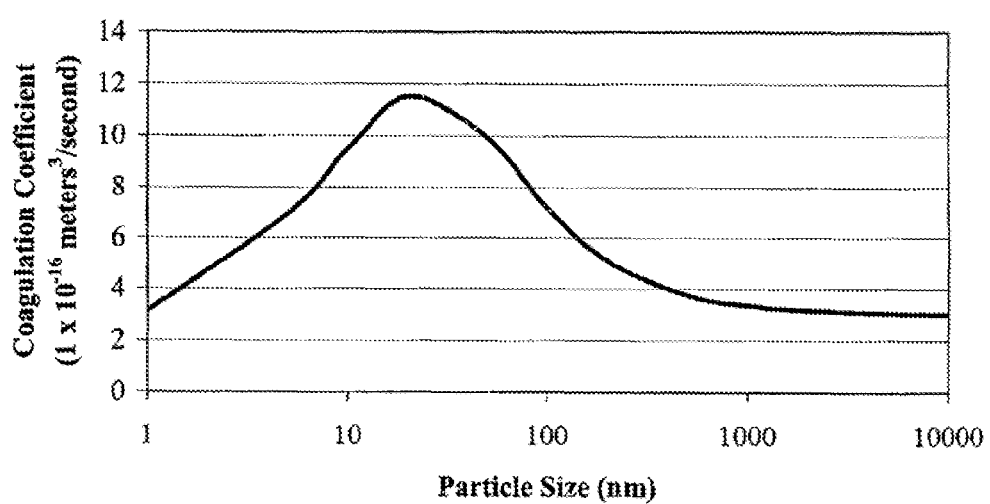
FIG. 24 is a plot of the coagulation coefficient (K) versus particle size of the compound.

FIG. 23 is for an aerosol having a Coagulation Coefficient (K) of $5 \times 10^{-16}$ meters$^3$/second. This K value corresponds to a particle size of 200 nm. As the particle size changes, so can its K value. Table 1 below gives the K values for various particle sizes. As K increases, the time required for the aerosol to aggregate from a particular particle size to a larger particle size is reduced. As can be seen from Table 1 and FIG. 24, when the particle is in the ultra fine region, as defined in the BACKGROUND OF THE INVENTION section, the effect of a changing K value tends to accelerate the coagulation process towards 100 nm in size. In calculating the stability of an aerosol's particle size, the size of the particle affects its stability. Smaller particles in this region will tend to aggregate faster than the larger sized particles. Therefore, the stability of particle size in the ultra fine range is not linear with dose size. In the fine particle size range, K remains fairly constant. Thus, the stability of particle size can be calculated from the dose size alone and consideration of particle size on the aggregation procession is unnecessary.

TABLE 1

| Particle size (diameter in nm) | Coagulation Coefficient ($\times e^{-15}$ meters$^3$/second) |
| --- | --- |
| 1 | 3.11 |
| 5 | 6.93 |
| 10 | 9.48 |
| 20 | 11.50 |
| 50 | 9.92 |
| 100 | 7.17 |
| 200 | 5.09 |
| 500 | 3.76 |
| 1000 | 3.35 |
| 2000 | 3.15 |
| 5000 | 3.04 |
| 10000 | 3.00 |

In creating an aerosol of a particular particle size, the ratio of mass of vaporized compound to the volume of the mixing gas is the controlling condition. By changing this ratio, the particle size can be manipulated (see FIG. 29). However, not all compounds and not all gases, with the same ratio will result in the same particle size distribution (PSD). Other factors must be known to be able to accurately predict the resultant particle size. A compound's density, polarity, and temperature are examples of some of these factors. Additionally, whether the compound is hydrophilic or hydrophobic will affect the eventual particle size, because this factor affects an aerosol's tendency to grow by taking on water from the surrounding environment.

In order to simplify the approach used to predict the resulting particle size, the following assumptions were made:
1. The compound is non polar (or has a weak polarity).
2. The compound is hydrophobic or hydrophilic with a mixing gas that is dry.
3. The resultant aerosol is at or close to standard temperature and pressure.
4. The coagulation coefficient is constant over the particle size range and therefore the number concentration that predicts the stability of the particle size is constant.

Consequently, the following variables are taken into consideration in predicting the resulting particle size:
1. The amount (in grams) of compound vaporized.
2. The volume of gas (in cc's) that the vaporized compound is mixed into.
3. The "stable" number concentration in number of particles/cc.
4. The GSD of the aerosol.

Predicting the particle size would be a simple matter for a given number concentration and amount of the compound, if the GSD is 1. With a GSD of 1, all of the particle sizes are the same size and therefore the calculation of particle size becomes a matter of dividing a compound's mass into the number of particles given by the number concentration and from there calculating the particle size diameter using the density of the compound.

The problem becomes different though if the GSD is other than 1. As an aerosol changes from a GSD of 1 to a GSD of 1.35, the mass median diameter (MMD) will increase. MMD is the point of equilibrium where an equal mass of material exists in smaller diameter particles as exists in larger diameter particles. Since total mass is not changing as the GSD changes, and since there are large and small particles, the MMD must become larger as the GSD increases because the mass of a particle goes up as the cube of its diameter. Therefore larger particles, in effect, carry more weight so the MMD becomes larger to "balance" out the masses.

To determine the effect of a changing GSD, one can start with the formula for the mass per unit volume of an aerosol given a known MMD, GSD, density, and number concentration. The formula is from Finlay's "*The Mechanics of Inhaled Pharmaceutical Aerosols*" (2001, Academic press). Formula 2.39 states that the mass per unit volume of an aerosol is:

$$M = (\rho N \pi / 6)(MMD)^3 \exp[-9/2(\ln \sigma_g)^2]$$

Where:
ρ=density in gm/cc
N=Number concentration in particles/cc
MMD=mass median diameter (in cm)
$\sigma_g$=the GSD
M=the mass per unit volume of the aerosol in gms/cc If the change in the MMD is considered as an aerosol changes from one GSD to another, while the density, number concentration, and the mass remain unchanged the following equality can be set up:

$$\rho N \pi / 6 (MMD_1)^3 \exp[-9/2(\ln \sigma_{g1})^2] = \rho N \pi / 6 (MMD_2)^3 \exp[-9/2(\ln \sigma_{g2})^2]$$

simplifying:

$$(MMD_1)^3 \exp[-9/2(\ln \sigma_{g1})^2] = (MMD_2)^3 \exp[-9/2(\ln \sigma_{g2})^2]$$

Or $$(MMD_1)^3 / (MMD_2)^3 = \exp[-9/2(\ln \sigma_{g2})^2] / \exp[-9/2(\ln \sigma_{g1})^2]$$

If one sets the GSD of case 1 to 1.0 then:

$$\exp[-9/2(\ln \sigma_{g1})^2] = 1$$

And therefore:

$$(MMD_1/MMD_2)^3 = \exp[-9/2(\ln \sigma_{g2})^2]$$

Or:

$$MMD_1/MMD_2 = \exp[-3/2(\ln \sigma_{g2})^2]$$

It is advantageous to calculate the change in the MMD as the GSD changes. Solving for $MMD_2$ as a function of $MMD_1$ and the new $GSD_2$ yields:

$$MMD_2 = MMD_1/\exp[-3/2(\ln \sigma_{g2})^2] \text{ for a } \sigma_{g1}=1$$

To calculate $MMD_1$, divide the compound's mass into the number of particles and then, calculate its diameter using the density of the compound.

$$MMD_1 = (6C/\rho NV)^{1/3} \text{ for an aerosol with a GSD of 1}$$

Where:
C=the mass of the compound in gm's
ρ=Density in gm/cc (as before)
N=Number concentration in particles/cc (as before)
V=volume of the mixing gas in cc Insertion of $MMD_1$ into the above equation leads to:
$$MMD_2 = (6C/\rho NV\pi)^{1/3}/[\exp[-3/2(\ln \sigma_{g2})^2], \text{ measured in centimeters.}$$

A resultant MMD can be calculated from the number concentration, the mass of the compound, the compound density, the volume of the mixing gas, and the GSD of the aerosol.

In all of the embodiments of the present invention, an aerosol of the desired particle size range is created by controlling the volume of air (or other gas) within which the compound is allowed to aggregate. For creating ultra fine particles, a large ratio of mixing gas to compound vapor is used. In producing fine particles, it is necessary to reduce the volume of the initial mixing gas, which leads to an increase in the concentration of the compound, which in turn results in a greater particle size growth before a desired number concentration is reached and aggregation slows. When a stable particle size is reached in a smaller total volume, the mixture is then injected into the balance of the air. As referred to in some of the embodiments, this initial mixing stage can be, if needed, accomplished in the presence of an inert gas to reduce decomposition resulting from oxidation.

It is important to recognize that an aerosol with a particle size of 100 nm will occupy a volume 8,000 times as large as an aerosol with a particle size of 2 microns with the same number concentration and with the same total dose. Because the present method will require vastly different volumes of mixing air depending on the particle size desired for different compounds and amounts to be delivered, the various embodiments of the present invention are of different physical sizes and geometries.

The required vaporization rate is different depending on the particle size one wishes to create. If the particle size is in the ultra fine region, then the compound, once vaporized, must be mixed, in most cases, into the largest possible volume of air. This volume of air is determined from lung physiology and can be assumed to have a reasonable upper limit of 2 liters. If the volume of air is limited to below 2 liters (e.g. 500 cc, unless the dose is exceedingly small, i.e., less that 50 μg, too large a particle will result and optimum lung deposition will not be possible.

In the ultra fine range, doses of 1-2 mg are possible. If this dose is mixed into 2 liters of air, which will be inhaled in 1-2 seconds, the required, desired vaporization rate is in the range of about 0.5 to about 2 mg/second. A reasonable vaporization rate for ultra fine aerosols is about 1 mg/second for the embodiments of this invention.

In the fine particle size region, there is no need for as large a volume of air as possible. Until the establishment of the correct number concentration that makes a stable aerosol, a large volume of air is undesirable. Rapid mixing of the vaporized compound into air needs to happen at the time of vaporization to minimize decomposition. As a result, the volume of mixing air and not the entire volume of air used to deliver the drug to the lung is of chief concern.

Figure 1:
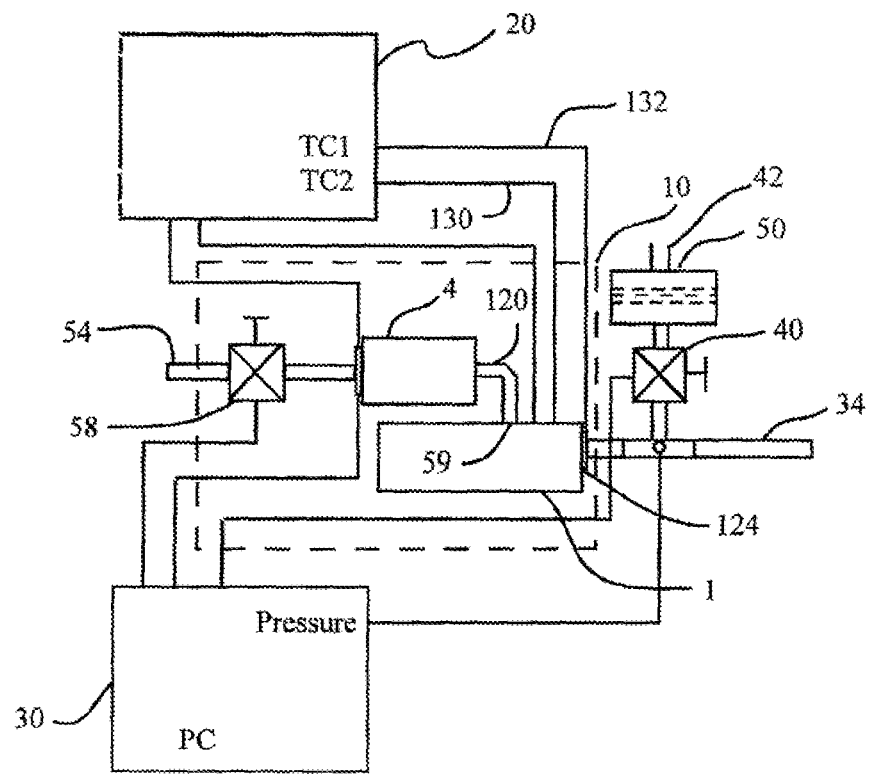
FIG. 1 is a schematic diagram of the overall system for conducting experiments using a laboratory device of the present invention.
Figure 2:
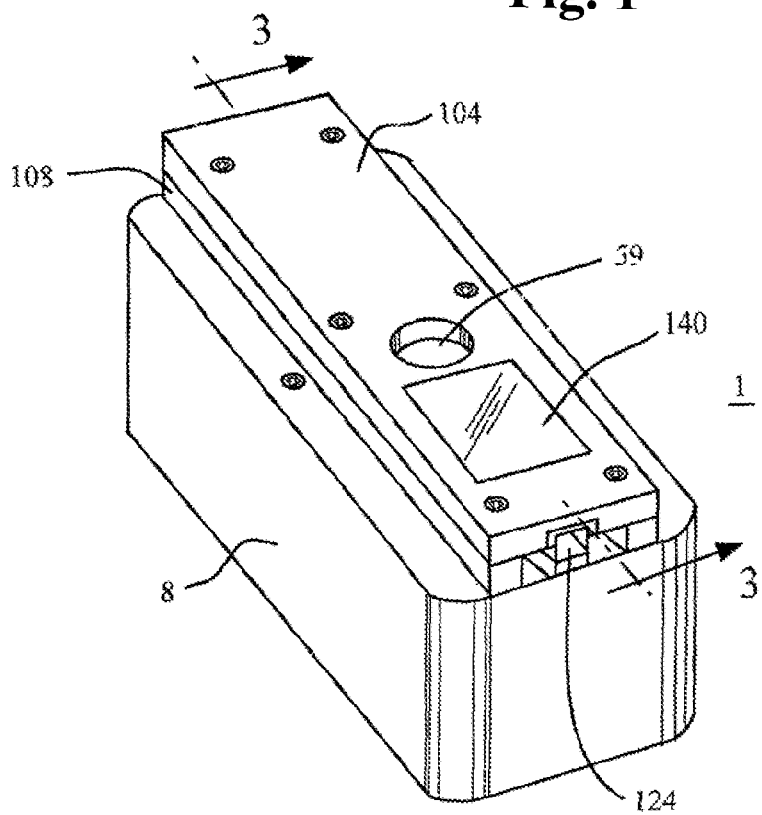
FIG. 2 is a top, right end and front perspective view of the actual laboratory device depicted in FIG. 1.

The first embodiment of the present invention is shown in FIG. 1 and is the basic device through which the principles cited above have been demonstrated in the laboratory. This device is described in detail in the EXAMPLES.

Figure 9:
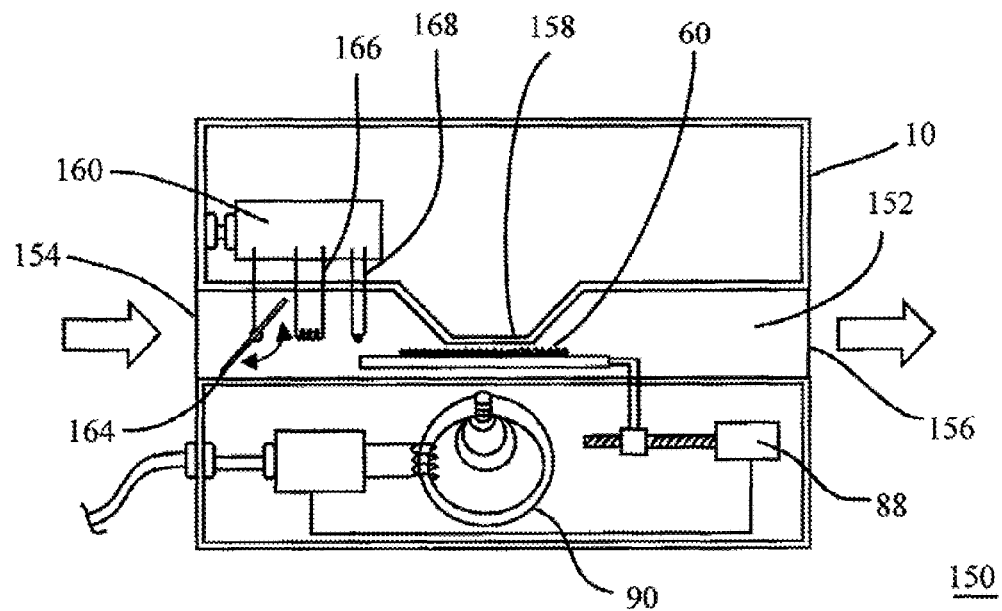
FIG. 9 is a schematic side view of a second embodiment of the present invention using a venturi tube.

In the second embodiment of the present invention shown in FIG. 9, the use of a reduced airway cross section increases the speed of the air across the compound's surface to about 10 meters/second. If complete mixing is to happen within 1 millisecond then the distance the gas and vaporized mixture must travel to achieve complete mixing must be no longer than 10 millimeters. However, it is more desirable for complete mixing to happen before the compound has aggregated to a larger size, so a desirable mixing distance is about 1 millimeter or less.

In the third embodiment of the present invention shown in FIGS. 10-13, an ultra fine aerosol is generated by allowing air to sweep over a thin film of the compound during the heating process. This allows the compound to become vaporized at a lower temperature due to the lowering of the partial pressure of the compound near the surface of the film.

Figure 14:
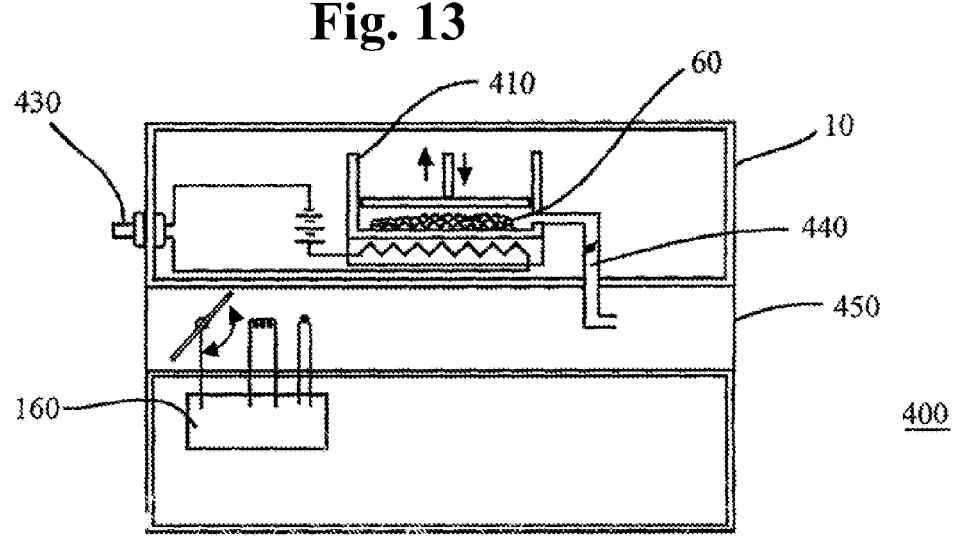
FIG. 14 is a schematic side view of a fourth embodiment of the present invention using an expandable container for the compound.
Figure 15:
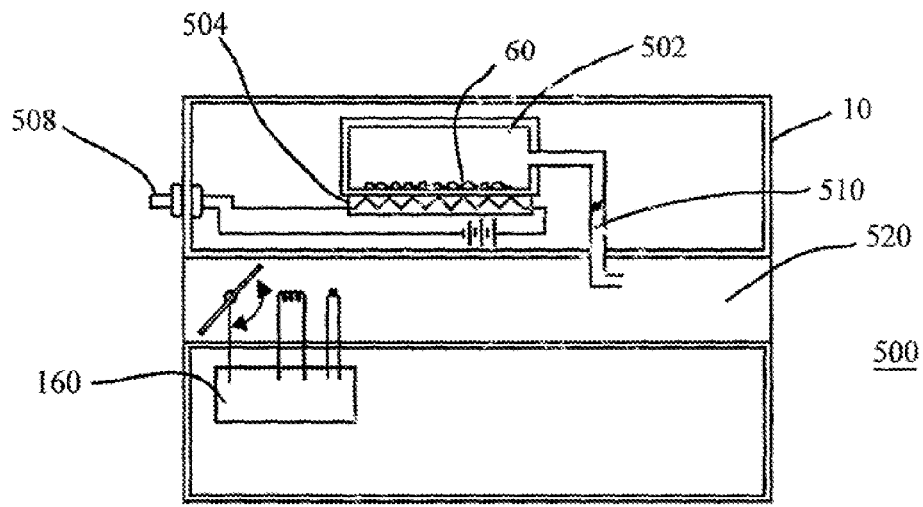
FIG. 15 is a schematic side view of a fifth embodiment of the present invention using a container for the compound in an inert atmosphere.
Figure 16:
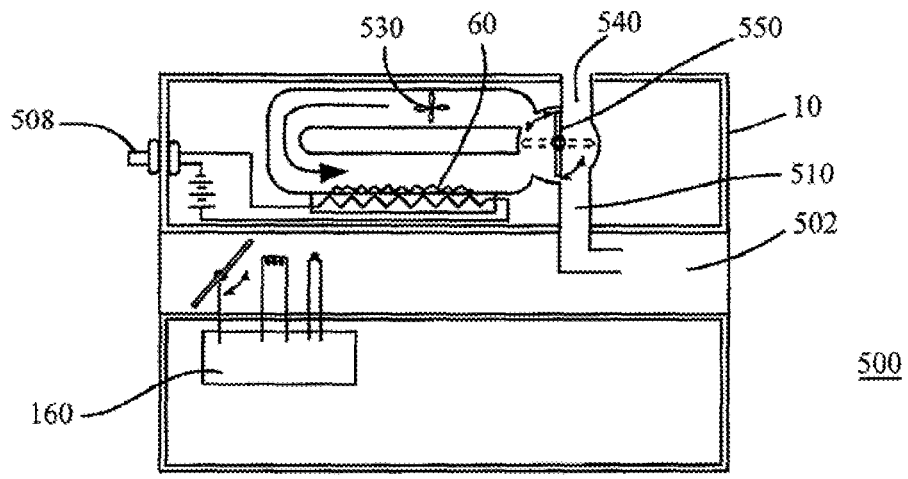
FIG. 16 is a schematic side view of the embodiment shown in FIG. 15 using a re-circulation of the inert atmosphere over the compound's surface.
Figure 19:
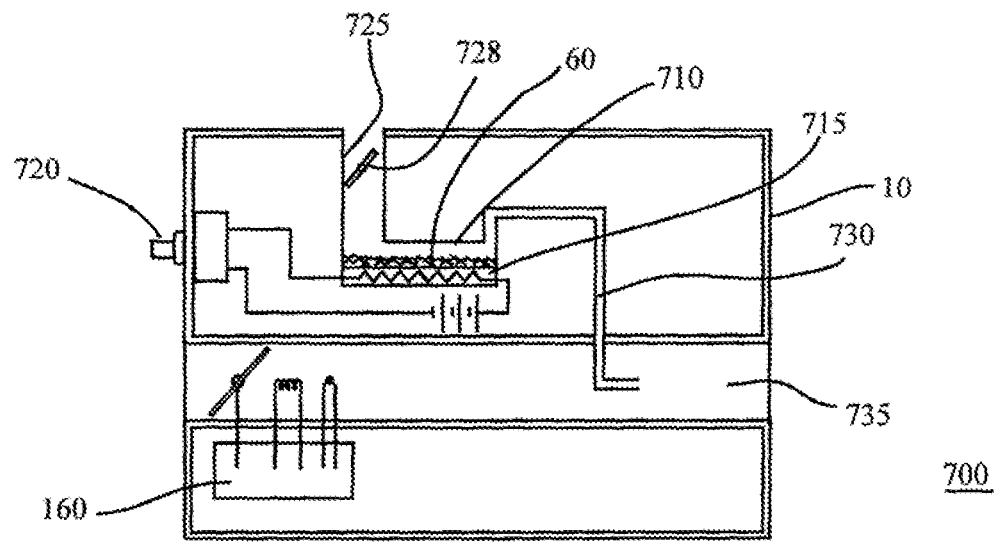
FIG. 19 is a schematic side view of a seventh embodiment of the present invention referred to herein as the "oven device"

The fourth embodiment shown in FIG. 14, the fifth embodiment shown in FIGS. 15 and 16, and the seventh embodiment shown in FIG. 19 overcome a problem with certain compounds that react rapidly with oxygen at elevated temperatures. To solve this problem, the compound is heated in an expandable container (fourth embodiment), a small container housing under a vacuum or containing a small amount, e.g., about 1 to about 10 ml, of an inert gas (fifth embodiment). Once a compound is vaporized and mixed with an inert gas while the gaseous mixture is maintained at a temperature sufficient to keep the compound in its vaporized state, the gaseous mixture is then injected into an air stream. The volume of inert gas can also be re-circulated over the surface of the heated compound to aid in its vaporization as shown in FIG. 16. In the seventh embodiment, the compound is introduced into the gas as a pure vapor. This involves vaporizing the compound in an oven or other container and then injecting the vapor into an air or other gas stream through one or more mixing nozzles.

Figure 17:
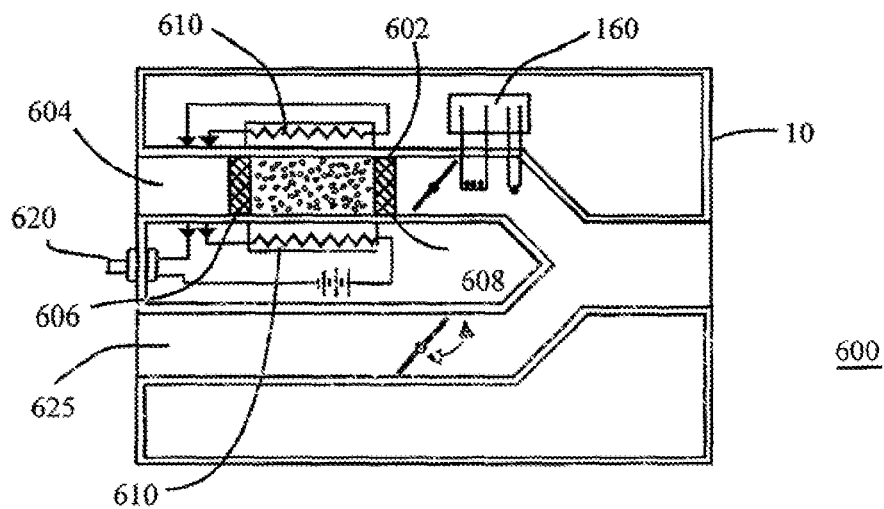
FIG. 17 is a schematic side view of a sixth embodiment of the present invention using a tube containing particles coated with the compound.
Figure 18:
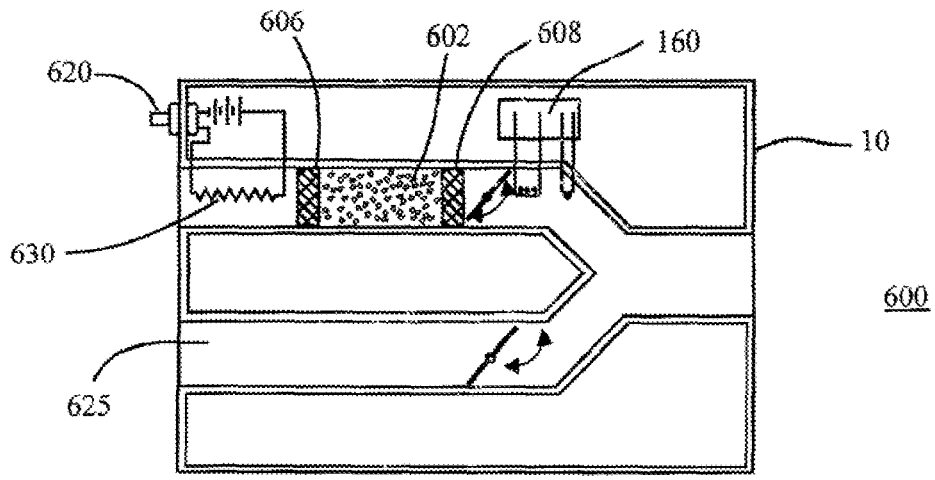
FIG. 18 is a schematic side view of the embodiment shown in FIG. 17 using a heating system to heat the gas passing over the coated particles.

In the sixth embodiment shown in FIGS. 17-18, gas is passed through a first tube and over discrete substrate particles, having a large surface area to mass ratio, and coated with the compound. The particles are heated as shown in FIG. 17 to vaporize the compound, or the gas is heated and the heated gas vaporizes the compound as shown in FIG. 18. The gaseous mixture from the first tube is combined with the gas passing through second tube to rapidly cool the mixture before administering it to a patient.

Figure 20:
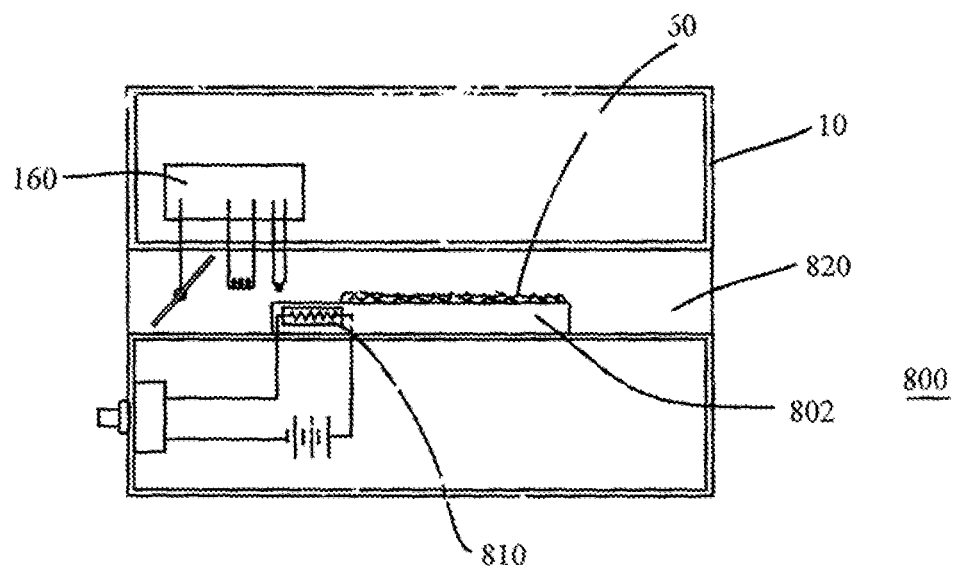
FIG. 20 is a schematic side view of an eighth embodiment of the present invention using gradient heating.

The eighth embodiment shown in FIG. 20 is a thermal gradient device that is similar to the preferred embodiment used in the laboratory experiments. This device also has a moving heating zone without any moving parts, accomplished by establishing a heat gradient that transverses from one end of the device to the other over time. As the heating zone moves, exposed portions of the compound are sequentially heated and vaporized. In this manner the vaporized compound can be introduced into a gas stream over time.

Figure 21:
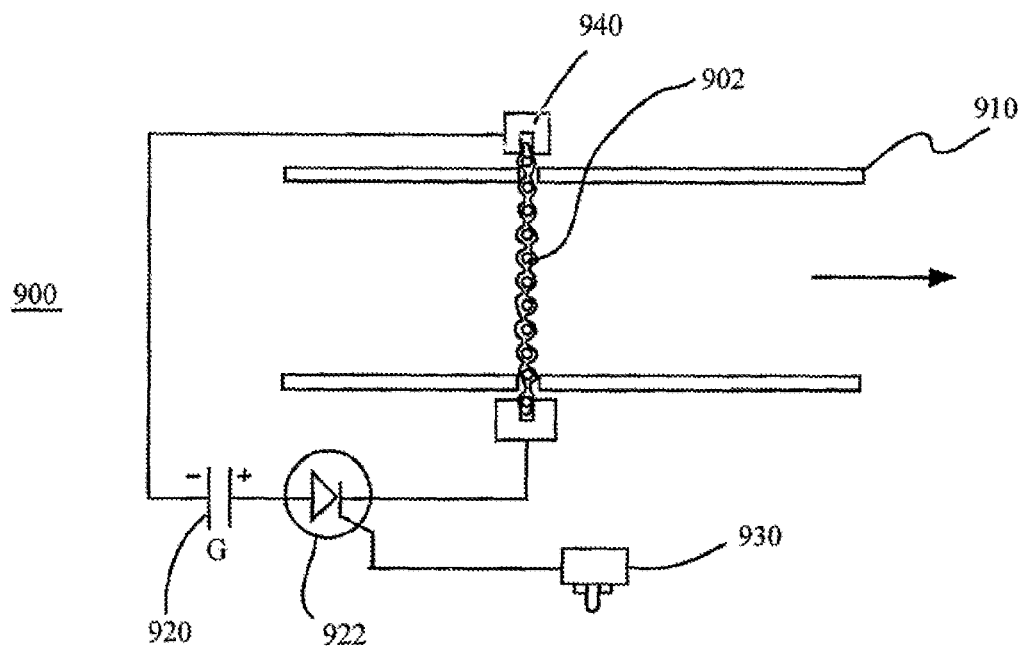
FIG. 21 is a schematic side view of a ninth embodiment of the present invention using a fine mesh screen coated with the compound.
Figure 22:
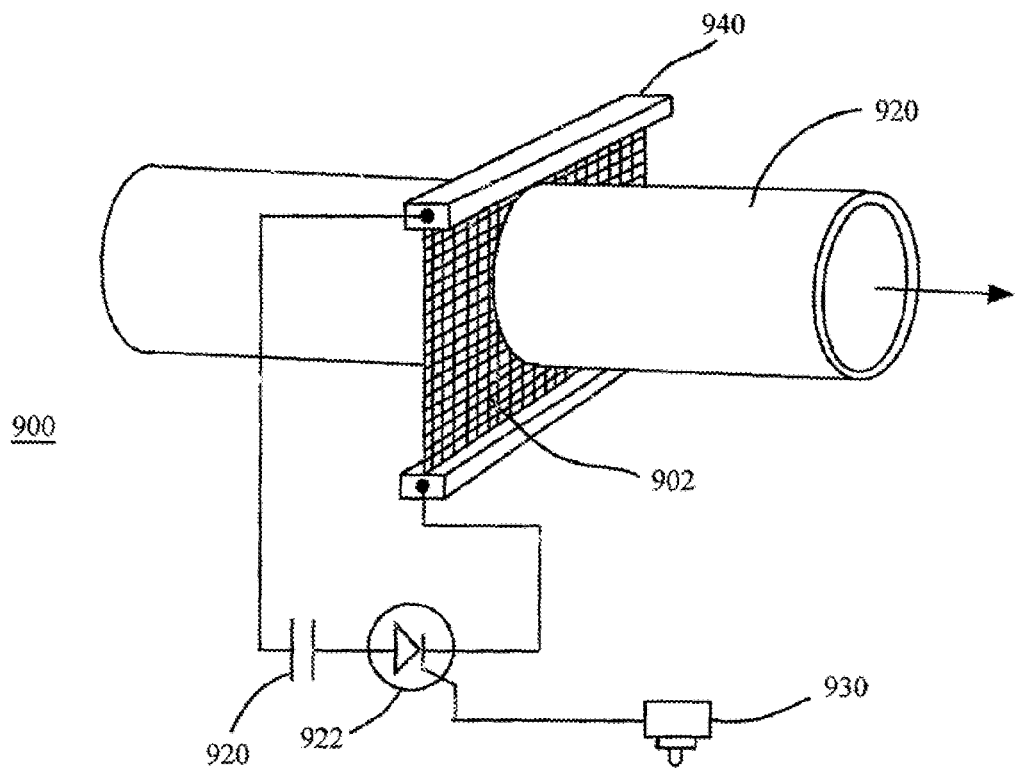
FIG. 22 is a top, right end and front perspective view of the embodiment shown in FIG. 21.

The ninth embodiment shown in FIGS. 21-22 is the screen device and is preferred for generating a fine aerosol. In this embodiment, air is channeled through a fine mesh screen upon which the drug to be administered to the patient has been deposited.

The embodiments above can create aerosols without significant drug decomposition. This is accomplished while maintaining a required vaporization rate for particle size control by employing a short duration heating cycle. An airflow over the surface of the compound is established such that when the compound is heated and reaches the temperature where vaporization is first possible, the resulting compound vapors will immediately cool in the air. In the preferred embodiments, this is accomplished by extending the increased velocity and mixing region over an area that is larger than the heating zone region. As a result, precise control of temperature is not necessary since the compound vaporizes the instant its vaporization temperature is reached. Additionally because mixing is also present at the point of vaporization, cooling is accomplished quickly upon vaporization.

Application of the present invention to human inhalation drug delivery must accommodate constraints of the human body and breathing physiology. Many studies of particle deposition in the lung have been conducted in the fields of public health, environmental toxicology and radiation safety. Most of the models and the in vivo data collected from those studies, relate to the exposure of people to aerosols homogeneously distributed in the air that they breathe, where the subject does nothing actively to minimize or maximize particle deposition in the lung. The International Commission On Radiological Protection (ICRP) models are examples of this. (See James A C, Stahlhofen W, Rudolph G, Egan M J, Nixon W, Gehr P, Briant J K, *The respiratory tract deposition model proposed by the ICRP Task Group, Radiation Protection Dosimetry,* 1991; vol. 38: pgs. 157-168).

However, in the field of aerosol drug delivery, a patient is directed to breathe in a way that maximizes deposition of the drug in the lung. This kind of breathing usually involves a full exhalation, followed by a deep inhalation sometimes at a prescribed inhalation flow rate range, e.g., about 10 to about 150 liters/minute, followed by a breath hold of several seconds. In addition, ideally, the aerosol is not uniformly distributed in the air being inhaled, but is loaded into the early part of the breath as a bolus of aerosol, followed by a volume of clean air so that the aerosol is drawn into the alveoli and flushed out of the conductive airways, bronchi and trachea by the volume of clean air that follows. A typical deep adult human breath has a volume of about 2 to 5 liters. In order to ensure consistent delivery in the whole population of adult patients, delivery of the drug bolus should be completed in the first 1-1½ liters or so of inhaled air.

As a result of the constraints placed on the various embodiments of the present invention due to their application in human inhalation drug delivery, a compound must be vaporized in a minimum amount of time, preferably no greater than 1 to 2 seconds. As discussed earlier, it is also advantageous, to keep the temperature of vaporization at a minimum. In order for a compound to be vaporized in 2 seconds or less and for the temperature to be kept at a minimum, rapid air movement, in the range of about 10 to about 120 liters/minute, needs to flow across the surface of the compound.

The following parameters are imposed in carrying out the best mode of the present invention, due to human lung physiology, the physics of particle growth, and the physical chemistry of the desirable compounds:

(1) The compound needs to be vaporized over approximately 1 to 2 seconds for creation of particles in the ultra fine range.

(2) The compound needs to be raised to the vaporization temperature as rapidly as possible.

(3) The compound, once vaporized, needs to be cooled as quickly as possible.

(4) The compound needs to be raised to the maximum temperature for a minimum duration of time to minimize decomposition.

(5) The air or other gas needs to be moved rapidly across the surface of the compound to achieve the maximum rate of vaporization.

(6) The heating of the air or other gas should be kept to a minimum, i.e., an increase of temperature of no greater than about 15° C. above ambient.

(7) The compound needs to be mixed into the air or other gas at a consistent rate to have a consistent and repeatable particle size.

(8) As the gas speed increases across the compound being vaporized, the cross sectional area through the device needs to decrease. Additionally as the surface area of the compound increases the heating of the gas increases.

The parameters of the design for one of the preferred embodiments shown in FIGS. 2-5, 7 and 8 are the result of meeting and balancing the competing requirements listed above. One especially important requirement for an ultra fine aerosol is that a compound, while needing to be vaporized within at least a 1-second period, also needs to have each portion of the compound exposed to a heat-up period that is as brief as possible. In this embodiment, the compound is deposited onto a foil substrate and an alternating magnetic field is swept along a foil substrate heating the substrate such that the compound is vaporized sequentially over no more than about a one second period of time. Because of the sweeping action of the magnetic field, each segment of the compound has a heat-up time that is much less than one second.

In the embodiment noted directly above, the compound is laid down on a thin metallic foil. In one of the examples set forth below, stainless steel (alloy of 302, 304, or 316) was used in which the surface was treated to produce a rough texture. Other foil materials can be used, but it is important that the surface and texture of the material is such that it is "wetted" by the compound when the compound is in its liquid phase, otherwise it is possible for the liquid compound to "ball" up which would defeat the design of the device and significantly change the volatilizing parameters. If the liquid compound "balls" up, the compound can be blown into and picked up by the airflow without ever vaporizing. This leads to delivery of a particle size that is uncontrolled and undesirable.

Stainless steel has advantages over materials like aluminum because it has a lower thermal conductivity value, without an appreciable increase in thermal mass. Low thermal conductivity is helpful because heat generated by the process needs to remain in the immediate area of interest.

Exemplary compounds that can be vaporized in accordance with the present invention include cannabinoid extracts from cannabis, THC, ketorolac, fentanyl, morphine, testosterone, ibuprofen, codeine, nicotine, Vitamin A, Vitamin E acetate, Vitamin E, nitroglycerin, pilocarpine, mescaline, testosterone enanthate, menthol, phencaramide, methsuximide, eptastigmine, promethazine, procaine, retinol, lidocaine, trimeprazine, isosorbide dinitrate, timolol, methyprylon, etamiphyllin, propoxyphene, salmetrol, vitamin E succinate, methadone, oxprenolol, isoproterenol bitartrate, etaqualone, Vitamin D3, ethambutol, ritodrine, omoconazole, cocaine, lomustine, ketamine, ketoprofen, cilazaprol, propranolol, sufentanil, metaproterenol, pentoxapylline, captopril, loxapine, cyproheptidine, carvediol, trihexylphenadine, alprostadil, melatonin, testosterone proprionate, valproic acid, acebutolol, terbutaline, diazepam, topiramate, pentobarbital, alfentanil HCl, papaverine, nicergoline, fluconazole, zafirlukast, testosterone acetate, droperidol, atenolol, metoclopramide, enalapril, albuterol, ketotifen, isoproterenol, amiodarone HCl, zileuton, midazolam, oxycodone, cilostazol, propofol, nabilone, gabapentin, famotidine, lorezepam, naltrexone, acetaminophen, sumatriptan, bitolterol, nifedipine, phenobarbital, phentolamine, 13-cis retinoic acid, droprenilamine HCl, amlodipine, caffeine, zopiclone, tramadol HCl, pirbuterol, naloxone, meperidine HCl, trimethobenzamide, nalmefene, scopolamine, sildenafil, carbamazepine, procaterol HCl, methysergide, glutathione, olanzapine, zolpidem, levorphanol, buspirone and mixtures thereof.

The present invention has unique advantages as a means of delivering drugs by inhalation to the human body. The FDA has expressed concern about airway hypersensitivity due to inhalation products (See G. Poochikian and C. M. Bertha, "Inhalation drug product excipients controls: significance and pitfalls" presented at RDD VII, 2000). The method and device of the present invention are capable of delivering pure drug vapor to the lung without the simultaneous delivery of formulation ingredients, which oftentimes comprise a significant portion of the mass delivered to the patient when other drug delivery methods and devices are utilized. Formulation ingredients often include propellants such as chlorofluorohydrocarbons, solvents such as ethanol, detergents such as Polysorbate 80, preservatives such as benzalkonium chloride or carrier particles such as lactose. The present invention has the advantage of not introducing such excipient molecules into the delicate tissues of the lungs. The ability to deliver pure drug is especially advantageous for drugs that must be administered chronically. This invention allows for the administration of water insoluble drugs to a mammal without the need for excipients or injection. This can be advantageous in treating diseases of the eye, mucosa, skin and broken-skin.

Another advantage comes from the ability of the present invention to produce an ultra fine aerosol. Approximately 50,000 times as many particles exist within a volume of ultra fine aerosol as exists in the same mass of a fine aerosol. Since each particle deposits on the membrane of the lung, a correspondingly greater number of deposition sites are created in the lungs and at each site less material has to be dissolved and transported into the blood stream. This may be important for improving the rate of absorption and thus the bioavailabilty of compounds, e.g., lipophilic compounds, and large molecules such as proteins, peptides and DNA. It is suspected that a portion of some drugs that have a slow absorption rate from the peripheral airways are assimilated by macrophages before they can be absorbed, leading to a low bioavailability despite efficient deposition. Increasing absorption rate through deposition of ultra fine particles would thus be advantageous.

EXAMPLES

The following examples further illustrate the method and various embodiments of the present invention. These examples are for illustrative purposes and are not meant to limit the scope of the claims in any way.

Example 1

In this example, the laboratory embodiment of the device of this invention, referred to as Absorption/Distribution/Metabolism/Excretion (ADME) device 1, was designed to deliver an experimental dose of fentanyl between 20 μg and 500 μg, in a range of ultra fine particle sizes, in about 800 cc of air to a 10 kg dog. The lung volume of each dog under experimentation was approximately 600-700 cc and the device was designed to deliver the compound to the lung in the first half of the inhalation. Because of the value of these parameters, ADME device 1 can be considered a ¼ scale device for administering a dose to a human. It is believed that scaling the device to work for human subjects involves mainly increasing the airflow through the device.

In this embodiment, representing one of the preferred embodiments of the present invention, the two main obstacles, decomposition and particle size control, as noted above, were addressed by moving a substrate that had the compound deposited on it into a heating/vaporization/mixing zone. The substrate material, which had been chosen in part for its electrical and thermal properties, was moved into an alternating magnetic field, which also coincided with a region of restricted cross-sectional area and mixing geometry. The alternating magnetic field induced an electrical current in the substrate and because of the substrate's electrical resistance resulted in a rapid temperature rise, which in turn vaporized the compound. The temperature rise occurred in a region where, because of the restriction of the cross-sectional area of the air channel, there was an increase in the air speed across the surface of the compound. The increased airflow acted to "sweep" away any compound vapors above the film of compound, which in turn lowered the partial pressure of the compound and increased the rate of vaporization.

Additionally, the temperature rise was also in a region where the geometry of the passage had been designed to promote rapid mixing of the vaporized compound into the air. This rapid mixing helped overcome the two noted obstacles in two ways. First, because of the rapid mixing there was a more uniform distribution of the compound into the air. This gave rise to a small distribution of particle sizes, which in turn insured a consistent and small particle size. Second, because rapid mixing occurred, the vaporized compound was rapidly cooled by exchange of its kinetic energy with kinetic energy of the cooler carrier air; which reduced decomposition.

The time frame of the introduction of the compound into the heating/vaporization/mixing zone was designed to vaporize the compound into a volume of air that was suitable for both the volume required by lung anatomy (600-700 cc) for the dog and the volume needed to control the ratio of the compound to the air, and thereby to control particle size. In other words, some of the functional limits for this device were defined by lung capacity as well as the requirements for dilution of the aerosol. Lung capacity limits the total amount of drug that can be suspended in the inhaled air at a given concentration.

The ADME device 1 as shown in FIG. 1 is operably connected to flow meter 4. In this example a TSI 4100 flow meter was used as the flow measuring equipment. The readings from flow meter 4 were fed to the electronics within chassis 8 shown in FIG. 2. It is noted that flow meter 4 is shown in FIG. 1 within a dotted line to indicate housing 10. For a practical device used to administer a drug to human patients, a flow meter will be included within a handheld housing. Device controller 20 includes Chembook model # N30W laptop computer having actuator switch 22 (FIG. 3) and National Instruments I/O Board (model #SC2345) that interfaces with computer 20 to control ADME device 1 and to control the recording of all data collected during the experiments. A software program to carry out these functions was developed using National Instruments' Labview software program. Connection between device 1 and the I/O board was accomplished with a DB25 cable (not shown). A standard "off the shelf" Condor F15-15-A+ power supply (not shown) delivered power to device 1. Inhalation controller 30 was used to control the rate and volume of inhalation through device 1 into the anesthetized dog through an endotracheal tube 34. Controller 30 had a programmable breath hold delay, at the end of which, exhaust valve 40 in exhaust line 42 opened and the dog was allowed to exhale. Filter 50 in line 42 measured the amount of exhaust and its composition to monitor any exhaled drug. The source air through inlet line 54, inlet valve 58, flow meter 4 and inlet orifice 59 was from a compressed air cylinder (not shown).

Now referring to FIGS. 3-5 and 7, the dose of compound 60 was deposited onto thin, stainless steel foil 64 so that the thickness of compound 60 was less than 10 microns. In most cases, compound 60 was deposited by making a solution of the compound with an organic solvent. This mixture was then applied to the foil substrate with an automated pump system. The size of the entire foil 64 was 0.7 by 2.9 inches and the area in which compound 60 was deposited was 0.35 by 1.6 inches.

Stainless steel (alloy of 302 or 304) foil 64 having a thickness of 0.004 inches was used for foil 64. Other foil materials can be used but stainless steel has an advantage over other materials like aluminum in that it has a much lower thermal conductivity value, while not appreciably increasing the thermal mass. A low thermal conductivity is helpful because the heat generated in foil 64 should stay in the area of interest, i.e. the heating/vaporization zone 70. Foil 64 needs to have a constant cross section, because without it the electrical currents induced by the heater will not be uniform.

Figure 7:
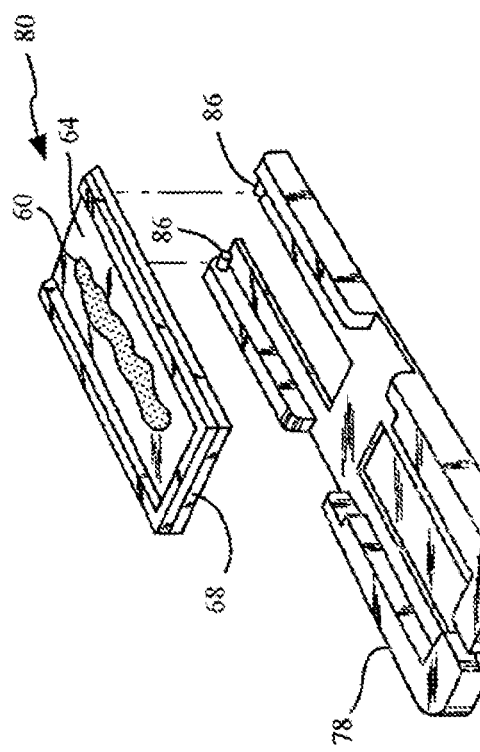
FIG. 7 is a top, left end and front perspective views of the removable sub-assembly containing the compound and a movable slide of the device shown in FIG. 2 showing the sub-assembly being mounted within the slide.

Foil 64 was held in frame 68, made so that the trailing edge of foil 64 had no lip on movable slide 78 and so compound 60, once mixed with the air, was free to travel downstream as seen in FIG. 7. Frame 68 was made of a non-conductive material to withstand moderate heat (200° C.) and to be non-chemically reactive with the compound. The material for frame 68 was Delrin AF, a copolymer of acetal and Teflon.

Sub-assembly 80 shown in FIG. 7 consists of frame 68 having foil 64 mounted therein and with compound 60 deposited on foil 64. Sub-assembly 80 was secured within movable slide 84 by setting each of the downstream ends of frame 68 that were tapered to abut against small rods 86 protruding from each downstream end of slide 78, as shown in FIG. 7. Slide 78 was driven by stepper motor 88 that moved sub-assembly 80 containing compound 60 along the axis of device 1. This, in turn, moved stainless steel foil 64 through an alternating magnetic field. It is preferable for the magnetic field to be confined within heating/vaporization zone 70 as in this laboratory embodiment. Ferrite 90 was used to direct the magnetic field and was placed approximately 0.05 inches below foil 64. In this laboratory embodiment designed to achieve the optimum results, heated area 70 was approximately 0.15 by 0.4 inches, with the smaller dimension along the direction of travel from left to right, i.e. from the upstream to the downstream ends of device 1, and the large dimension across the direction of travel, i.e., the width of device 1.

Stainless steel foil 64 functions as both a substrate for the drug to be delivered to the subject and the heating element for the vaporization of the drug. Heating element 64 was heated primarily by eddy currents induced by an alternating magnetic field. The alternating magnetic field was produced in ferrite toroid 90 with slit 94, which was wrapped with coil 98 of copper magnet wire. For this preferred embodiment, a ferrite toroid from the Fair-Rite Company was used. The slit was 0.10 inch wide. When an alternating current was passed through coil 98, an alternating magnetic field was produced in ferrite 90. A magnetic field filled the gap formed by slit 94 and magnetic field fringe lines 100 extended out from the toroid. The magnetic field line fringes intersected stainless steel heating element 64. When using a ferrite core, the alternating frequency of the field was limited to below 1 MHz. In this laboratory device, a frequency between 100 and 300 kHz was used. As alternating magnetic field lines 100 pass through foil 64, an alternating electric field was induced following Faraday's Law of Induction. The electric field caused eddy currents in the foil according to Ohm's law. The current moving through the intrinsic resistance of the foil generated the heat.

It is important to consider skin depth when inductively heating thin foils. If skin depth is much greater that the thickness of the foil, the magnetic field will pass through the foil and induce little heating. For a given frequency and material, the skin depth of a magnetic field can be determined using Formula #3 below:

$$\delta = \sqrt{\frac{2\varepsilon_0 c^2}{\sigma \omega}}$$

(Ref. The Feynman Lectures on Physics, vol. 2, pg. 32-11 Addison Wesley 1964)

Where:
- $\varepsilon_o$ is the permittivity of free space ($8.85 \times 10^{-12}$ farad/meter)
- c is the speed of light ($3 \times 10^8$ meters/second)
- σ is the conductivity of the foil ($1.38 \times 10^6$ 1/ohm-meters for stainless steel)
- ω is the frequency of the alternating magnetic field in radians/second.

The thicker the stainless steel foil used, the better the coupling of the magnetic field into the foil. However, more energy is needed to achieve a given temperature rise. Therefore, for a practical implementation of the device described above, a number of factors must be considered. First, the very thin foils that require less energy to raise them to a given temperature are less able to absorb the magnetic field due to the skin effect. Second, the ferrite is limited in its ability to conduct magnetic flux. The ferrite has both a saturation limit and internal power loses due to magnetic hysteresis. Foil thickness, ferrite material properties and geometry and operating frequency must be traded off to optimize the transfer of energy from the magnetic components to the foil.

The location and geometry of the eddy currents are also important since they determine where foil 64 will be heated. Since magnetic field fringe lines 100 pass through foil 64 twice, once leaving ferrite toroid 90 and once returning, two rings of current were produced, and in opposite directions. One of the rings was formed around magnetic field lines 100 that leave toroid 90 and the other ring formed around magnetic field lines 100 that return to the toroid. The rings of current overlapped directly over the center of slit 94. Since they were in opposite directions, they sum together. The greatest heating effect was produced over the center of slit 94.

Figures 3, 4:
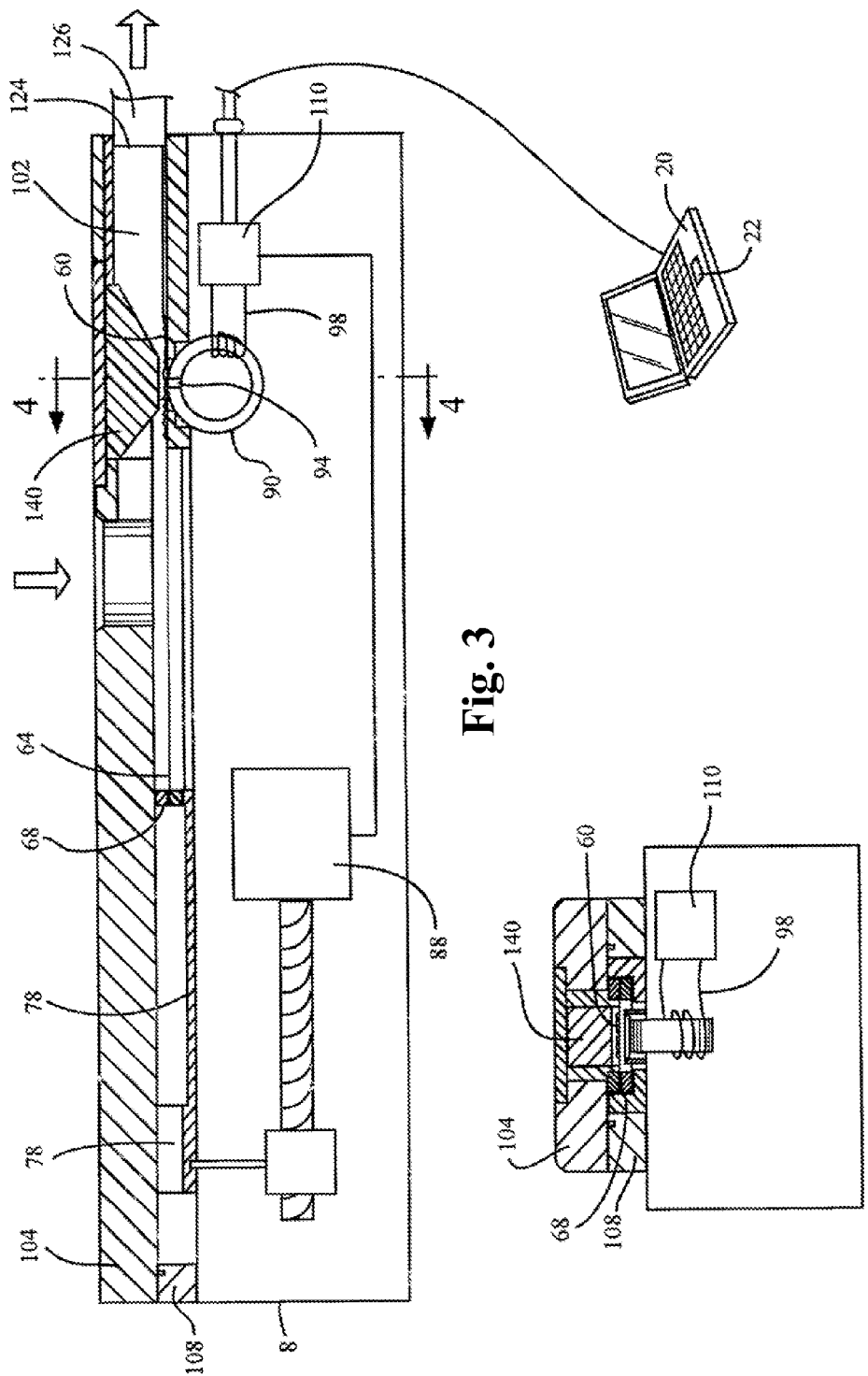
FIG. 3 is a partial cross-sectional and partial schematic side view of the device shown in FIG. 2.
FIG. 4 is a partial cross-sectional and partial schematic end view of the device shown in FIG. 2.
Figure 5:
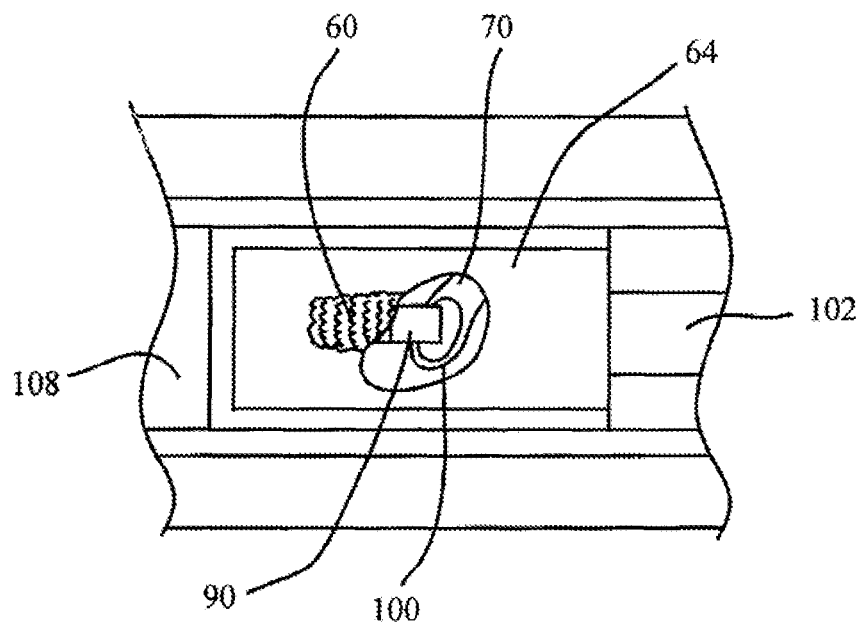
FIG. 5 is a partial cross-sectional and partial schematic top view of the device shown in FIG. 2.

Slide 84 and its contents, were housed in airway 102 made up of upper airway section 104 and lower airway 108 shown in FIG. 3. Upper airway section 104 was removable and allowed the insertion of movable slide 84 and then sub-assembly 80 of frame 78 and foil 64 with compound 60 on it and the removal of sub-assembly 80 after the dose had been administered. Lower airway section 108 was mounted on top of chassis 8 that housed the electronics, magnetic field generator 110, stepper motor 88 and position sensors (not shown). Mounted in upper airway section 104 was upstream passage 120 and inlet orifice 59 that coupled upper airway section 104 to flow meter 4. The readings from the flow meter 4 were fed to the electronics housed in chassis 8. Additionally, at the downstream end of airway passage 102 was outlet 124 connected to mouthpiece 126. Under test conditions, air was pulled through the mouthpiece 126 through airway tube 102 and inlet orifice 59. During administration of compound 60 to the dog, when joined to the system, air was forced through flow meter 4, inlet line 54, airway tube 102, and outlet 124 into the dog.

Additionally, a pyrometer at the end of TC2 line 130 was located within airway 102 and was used to measure the temperature of foil 64. Because of the specific geometry of ADME device 1, the temperature reading of foil 64 was taken after heating zone 70. Calibration of the thermal decay between heating zone 70 and the measurement area was required. Temperature data was collected and used for quality control and verification and not to control any heating parameters. A second temperature sensor was located at the end of TC1 line 132 in outlet 124 and was used to monitor the temperature of the air delivered to the dog.

In a preferred embodiment of the experimental device, removable airway section 140 contained a restricted cross-sectional area along with specific mixing geometry mounted in upper airway section 104. In this preferred embodiment, airway 140 lowered the roof of upper airway section 104 to within 0.04 inch of foil 64. Additionally, airway section 140 contained 31 steel rods (not shown) 0.05 inches in diameter. These rods were oriented perpendicular to the foil and extended from the "roof", i.e., the top of upper airway section 104, to within 0.004 inches of the foil. The rods that were placed in a staggered pattern had sharp squared off ends, which caused turbulence as the air was draw around them. Rapid, highly turbulent movement of mixing air resulted, which assured complete mixing of the vapor with the air passing through the device.

FIG. 9 schematically represents device 150, the second embodiment of the present invention, in which the cross-sectional area was also restricted along the gas/vapor mixing area. In this embodiment, venturi tube 152 within housing 10 having inlet 154, outlet 156 and throat 158 between inlet 154 and outlet 156 was used to restrict the gas flow through venturi tube 152. Controller 160 was designed to control the flow of air passing through valve 164 based on readings from the thermocouple 168 of the temperature of the air as a result of heater 166.

Airway section 140 was located directly over heating zone 70 and created a heating/vaporization/mixing zone. Prior to commencing aerosol generation, slide 78 was in the downstream position. Slide 78, with its contents, was then drawn upstream into this heating/vaporization/mixing zone 70 as energy was applied to foil 64 through the inductive heater system described in detail below.

Figure 6:
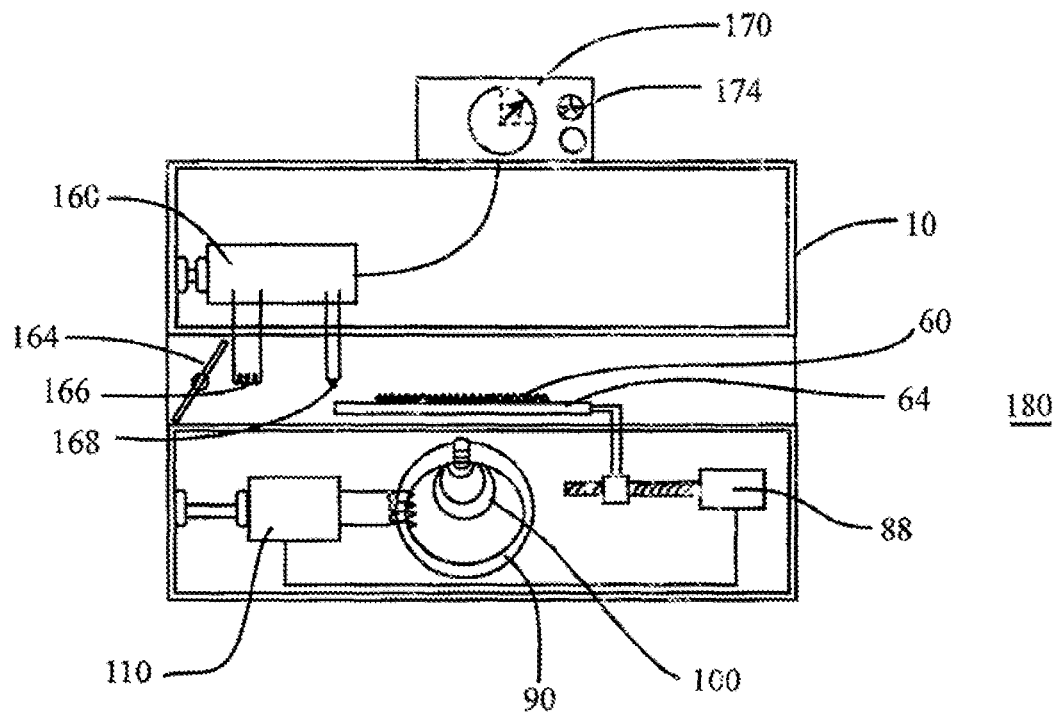
FIG. 6 is a schematic cross-sectional side view of an alternate embodiment of the device of the present invention using an annunciating device.

The device of the present invention can be equipped with an annunciating device. One of the many functions for the annunciating device is to alert the operator of the device that the compound is not being vaporized or is being improperly vaporized. The annunciating device can also be used to alert the operator that the gas flow rate is outside a desired range. Annunciating device 170 with on-off switch 174 is schematically represented in FIG. 6 for use with hand held device 180. During the use of device 180 in which the patient's inhalation rate controls the airflow rate, a signal from annunciating device 170 would alert the patient to adjust the inhalation rate to the desired range. In this case, controller 160 would be connected to annunciating device 170 to send the necessary signal that the flow rate was not within the desired range.

Figure 8:
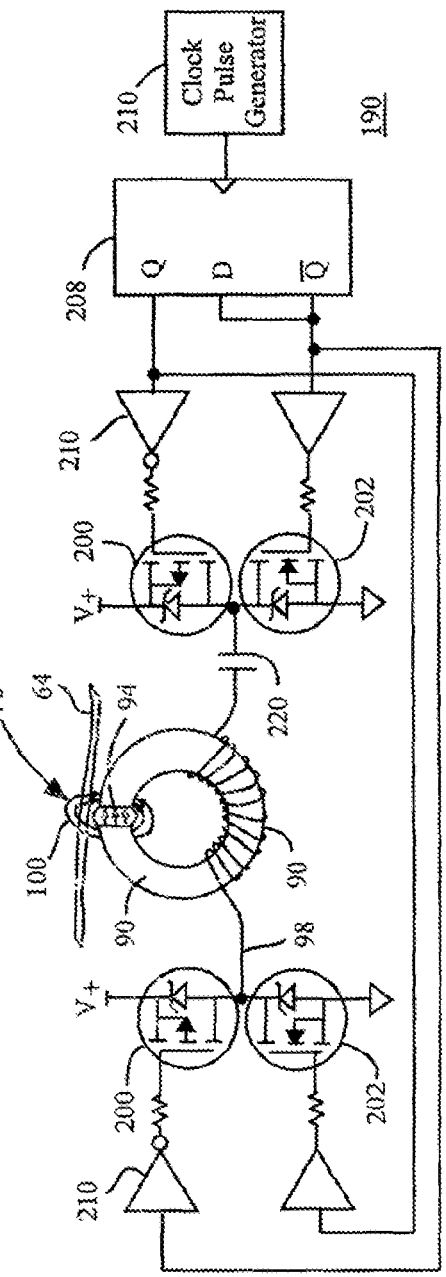
FIG. 8 is a schematic view of the heating element of the embodiment shown in FIG. 2 showing the electric drive circuit.

The induction drive circuit 190 shown in FIG. 8 was used to drive the induction-heating element of ADME device 1. The purpose of circuit 190 was to produce an alternating current in drive coil 98 wrapped around ferrite core 90. Circuit 190 consisted of two P-channel transistors 200 and two N-channel MOSFET transistors 202 arranged in a bridge configuration. MOSFET transistors 200 and 202 connected to clock pulse generator 219 were turned on and off in pairs by D-type flip-flop 208 through MOSFET transistor drive circuit 210. D-type flip-flop 208 was wired in such a way as to cause the Q output of the flip-flop to alternately change state with the rising edge of the clock generation signal. One pair of MOSFET transistors 200 was connected to the Q output on D-type flip-flop 208 and the other pair, 202, is connected to the Q-not output of flip-flop 208. When Q was high (5 Volts), a low impedance connection was made between the D.C. power supply (not shown) and the series combination of drive coil 98 and the capacitor through the pair of MOSFET transistors 200 controlled by the Q output. When D-type flip-flop 208 changed state and Q-not was high, the low impedance connection from the power supply to the series combination drive coil 98 and capacitor 220 was reversed. Since flip-flop 208 changes state on the rising edge of the clock generation signal, two flip-flop changes are required for one complete drive cycle of the induction-heating element. The clock generation signal was set at twice the resonant frequency of the series combination of drive coil 90 and capacitor 220. The clock signal frequency can be manually or automatically set.

The following was the sequence of events that took place during each operation:

1. At the beginning of the run, the operator triggered inhalation controller 30 to start monitoring data from pressure transducer 240 and input flow meter 4.
2. Controller 30 signaled controller 20 to start ADME device 1 and to begin collecting data from the two temperature sensors and flow meter 4.
3. After a pre-programmed delay, device 1 initiated the generation of the aerosol. (Note: there was a delay of about 0.4 seconds between the start of the controller 30 and the start of aerosol generation.)
4. After an independent preprogrammed delay (from original trigger signal), controller 30 opened input valve 58 to start forced inhalation to a dog under experimentation.
5. Device 1 completed the aerosol generation during the inhalation.
6. Controller 30 monitored flow meter 4 and pressure transducer 240 throughout the inhalation and closed off flow at input valve 58 when a pre-specified volume or pressure was met. (Note: the pre-specified pressure is a safety feature to prevent injury to the subject animal. Termination of the breath at the pre-specified volume is the desirable occurrence of the experiment.)
7. After a breath hold delay (5 seconds), exhaust valve 40 was opened and the dog was allowed to exhale.
8. Exhaled aerosol was trapped on exhaust filter 40 for later analysis. Controller 30 recorded values for the following: volume dispensed, terminal pressure, duration of air pulse, and average flow rate. Controller 20 continuously recorded at millisecond resolution, input flow rate, exhaust flow rate, foil temperature, mouthpiece temperature, slide position, heater on/off time, and other internal diagnostic electrical parameters.

In Vivo Results of the ADME Device 1 Embodiment

Three weight-matched female beagle dogs received fentanyl at a 100 μg intravenous bolus dose. The same dogs received fentanyl UF for Inhalation (100 μg aerosolized and administered as two successive activations of an ADME device 1, containing approximately 50 μg fentanyl base) at a particle size of 80 nm (MMAD). The aerosol was administered to anesthetized dogs via the system schematically represented in FIG. 1, with a target delivered volume of 600-700 ml air, followed by a 5 second breath hold. After dosing, plasma samples for pharmacokinetic analysis were obtained at various time points from 2 min to 24 hr. Fentanyl remaining in the dosing and administration apparatus 1 was recovered and measured. Fentanyl concentrations were measured by using a validated GC method, with a limit of detection of 0.2 ng/ml.

Plasma pharmacokinetics from this example was compared to intravenous (IV) fentanyl (100 μg) in the same dogs. Inhalation of fentanyl resulted in rapid absorption (Cmax, maximum concentration in plasma, 11.6 ng/ml and Tmax, maximum time, 2 min.) and high bioavailability (84%). The time course of inhaled fentanyl was nearly identical to that of IV fentanyl. Thus, fentanyl UF for inhalation had an exposure profile that was similar to that of an IV injection.

The use of fentanyl to demonstrate the utility of the preferred embodiment is significant for several reasons. First, the liver extensively metabolizes fentanyl. Thus, an oral dosage form of fentanyl would tend to be less effective because the drug must be absorbed from the gastrointestinal tract and then delivered to the liver. Either an IV dose or an inhalation dose of fentanyl travels directly from its site of entry, a vein in the case of an IV or to the lung in the case of the present invention, to the brain, its primary site of action, before it passes through the liver. The administration of fentanyl to patients is currently provided in several dosage forms: intravenous, transdermal and transmucosal. The latter consists of a matrix of fentanyl citrate on a stick (Actiq® oral transmucosal fentanyl citrate). The product literature provided for Actiq indicate that 25% of the dose is absorbed from the buccal mucosa while the remaining 75% is swallowed with the saliva and is then slowly absorbed from the gastrointestinal tract. About ⅓ of this amount (25% of the total dose) escapes hepatic and intestinal first-pass elimination and becomes systemically available. Thus, a significant advantage of the delivery system of the present invention is that it provides a means for rapid absorption of drugs such as fentanyl into the blood system for delivery directly to the brain, without the use of needles or excipients and without being exposed to a first pass metabolism in the gastrointestinal tract or liver.

Standard non-compartmental pharmacokinetic methods were used to calculate pharmacokinetic parameters for each animal. The maximum concentration in plasma (Cmax) and the maximum time it occurred (Tmax) were determined by examination of the data. The area under the plasma concentration vs. time curve (AUC) was determined. The bioavailability (F) of inhaled fentanyl was determined as:

$$F=(DIV/DINHAL)*(AUCINHAL/AUCIV)$$

Where D was the dose and AUC was the AUC determined to the last measurable time point.

Figure 26:
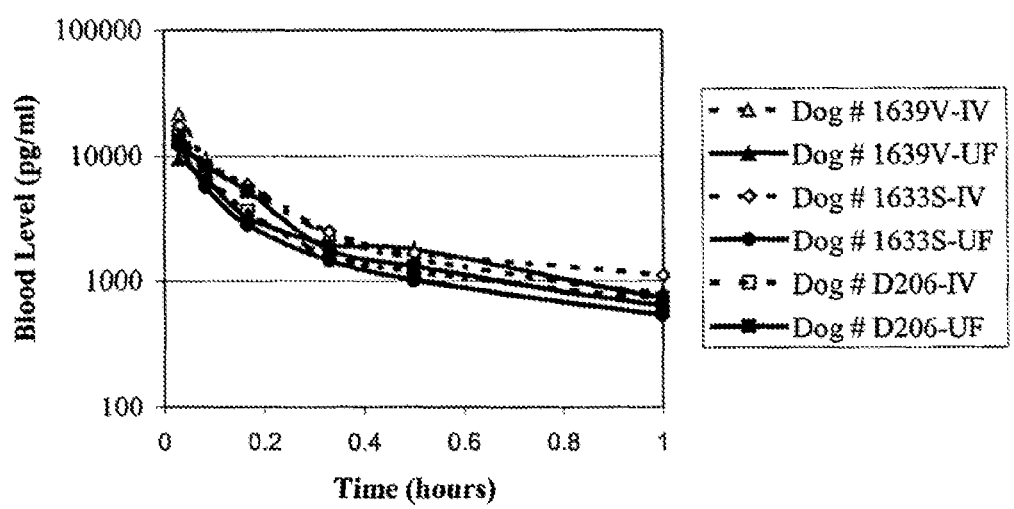
FIG. 26 is a plot of blood levels for both the IV dose and the inhalation dose administered to various dogs during the experiments using the system shown in FIG. 1.

FIG. 26 plots the data obtained on the blood levels, by dog, for both the IV doses and the inhalation doses using device 1 as described above under Example 1.

The fentanyl aerosol was rapidly absorbed, with the same Tmax (2 min, the earliest time point) observed for both routes of administration. The maximum plasma concentration of fentanyl aerosol (11.6±1.9 ng/ml) was nearly two-thirds that of IV fentanyl (17.6±3.6 ng/ml). Plasma concentrations fell below the assay limit of quantitation by 6-8 hr after IV administration and by 3-4 hr after aerosol inhalation. Bioavailability calculations were based on the AUC's observed to the last measurable time point for the inhalation administration. Bioavailability for the inhalation study was 84% based on the nominal (uncorrected) fentanyl dose.

The mean plasma elimination half-life was similar after IV (75.4 min) and inhalation dose. Distribution phase half-lives (3-4 min) were also similar after both routes of administration. The inter-animal variability of pharmacokinetic parameters after the inhalation dose was low, with relative standard deviations (RSD<25%) lower than those observed for IV administration.

In Vitro Results: ADME Device 1 Embodiment

Table 2 below summarizes the data collected from use of ADME device 1 for in vitro testing of fentanyl. Particle size was measured with a Moudi cascade impactor.

TABLE 2

| Compound Mass (ug) | Mixing air volume (cc) | MMAD (nm) | GSD |
|---|---|---|---|
| 20 | 400 | 71 | 1.9 |
| 25 | 400 | 72-78 | 1.7-1.8 |
| 50 | 400 | 77-88 | 1.7-185 |
| 100 | 400 | 100-105 | 1.4-1.8 |
| 200 | 400 | 103-123 | 1.6-1.9 |
| 300 | 400 | 140-160 | 1.8-2.1 |

Figure 27:
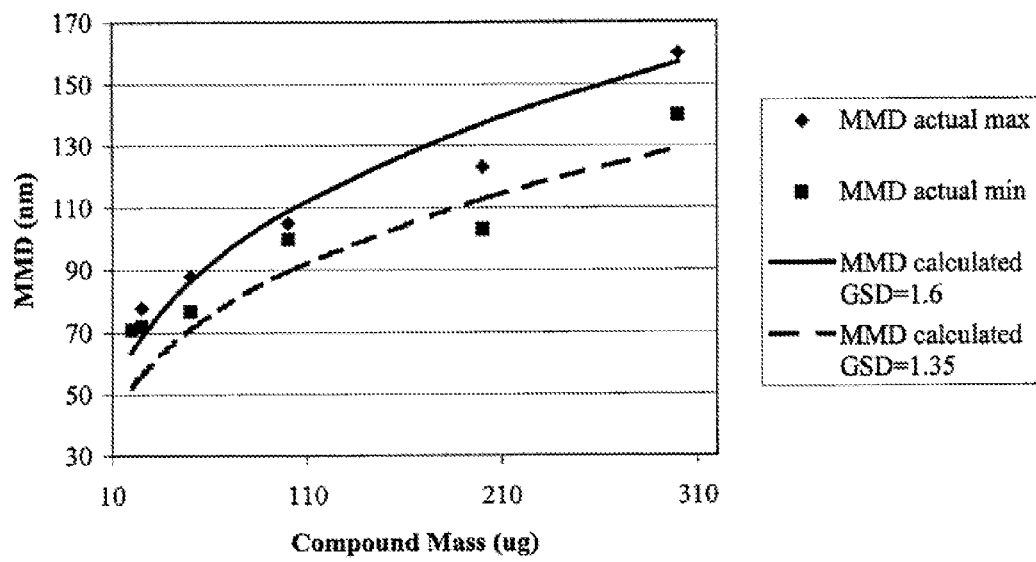
FIG. 27 is a plot of calculated and experimental mass median diameter (MMD) versus compound mass in the range of 10 to 310 µg.

FIG. 27 compares the MAD calculated value for a GSD equal to 1.35 and 1.60 to actual data on MAD summarized in Table 2 for ADME device. The distinction between MMAD (Mass Mean Aerodynamic Diameter; the diameter of a particle of unit density material that exhibits the same aerodynamic behavior as the measured aerosol) and MMD (Mass Mean Diameter; the diameter of a unit density particle) is ignored since the density of fentanyl is very close to 1 gm/cc. The calculated values for MMD are discussed above in section A of the DETAILED DESCRIPTION.

Figure 28:
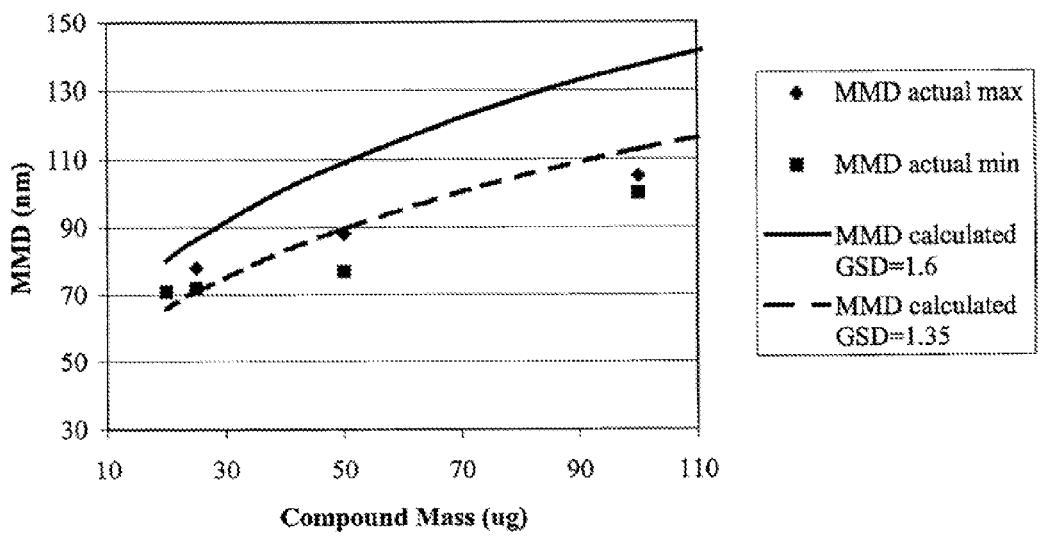
FIG. 28 is a plot of calculated and experimental MMD versus compound mass in the range of 10 to 310 µg.

The curves of FIG. 27 demonstrate a good correlation between the theoretical model based on the equations set forth earlier and actual data. Note that the theoretical prediction for small particles is less than the actual data. The reason, as stated earlier, is that when particle size becomes less than 80 nm the coagulation coefficient gets larger. As this happens a stable number concentration is reached at a lower number. If the calculation of MMD is redone with a number concentration of $0.5 \times 10^9$/cc instead of $1.0 \times 10^9$/cc, as used above, the curves shown in FIG. 28 result. As can be seen, the actual data fits the calculated data much better for the small particle sizes.

Example 2

In this example, ADME device 1 was slightly modified and the flow rate changed, as discussed below, to make a fine aerosol in the 1 to 3 micron particle size range.

Airway section 140 was removed and the air channel heating/vaporization zone 70 was changed. An airway insert (not shown) had a "roof" that was 0.25 inches above the foil. There were no mixing rods as rapid mixing was not desirable in this example. Because of these two device changes, there was much less mixing with the air, thus the vapor/aerosol cloud was mixed with less air and produced a larger particle size aerosol.

The airflow rate was reduced from 15 liters/minute in Example 1 to 1 liter/minute in this example. Again, this allowed the vapor to be mixed with much less air, resulting in the larger particle size aerosol.

Some operational problems with high compound loading on foil 64 in ADME device 1 were encountered. The compound tested, dioctyl phthalate (DOP), was an oil and during the aerosolization process, a substantial quantity was blown downwind and not aerosolized. Three additional design alternatives were made to address this issue, involving changes to the substrate surface that the compound was deposited on. In the three alternatives, the substrate was made to "hold" the compound through the use of texture. They were:

a. Texturing the foil.
   b. Adding a stainless steel screen on top of the foil.
   c. Replacing the foil with a fine stainless steel screen The results from this example are set forth below in Table 3 below:

TABLE 3

| Substrate Type | MMAD, microns | GSD | Emitted Dose, ug |
|---|---|---|---|
| Textured foil | 1.49 microns | 1.9 | 97 |
| Textured foil | 2.70 microns | 1.95 | 824 |
| Fine screen alone | 1.59 microns | 1.8 | 441 |
| Fine screen alone | 1.66 microns | 1.8 | 530 |
| Screen on Foil | 2.42 microns | 2.2 | 482 |

As shown above, a fine particle size can be made with ADME device 1 merely by changing the ratio of the compound to the mixing air.

Example 3

Figure 10:
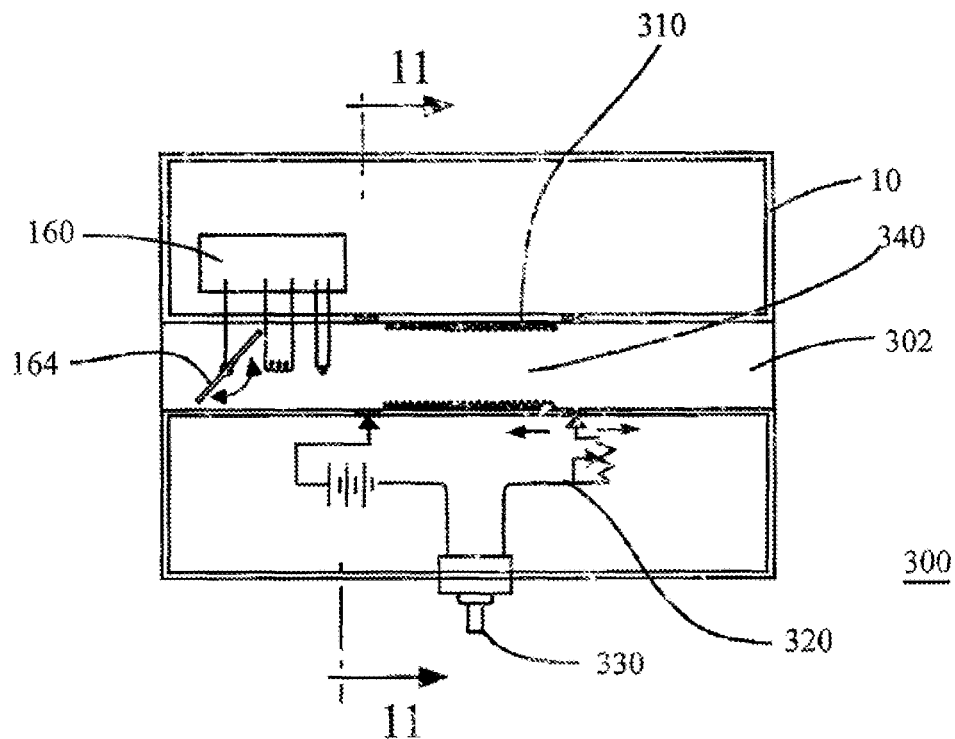
FIG. 10 is a schematic side view of a third embodiment of the present invention using a thin-walled tube coated with the compound.
Figure 11:
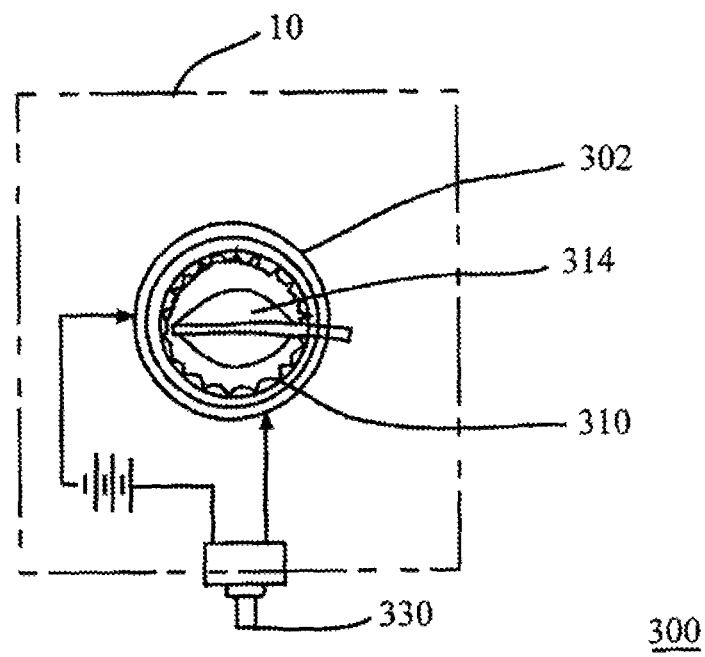
FIG. 11 is a schematic side end view of the embodiment shown in FIG. 10.
Figure 12:
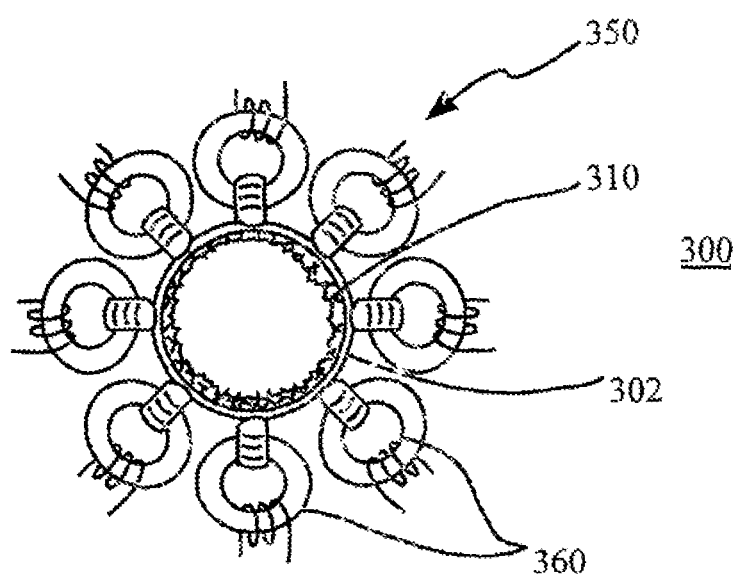
FIG. 12 is a schematic side end view of the embodiment shown in FIG. 10 showing an inductive heating system generating an alternating magnetic field.

In this example, device 300, the third embodiment of the present invention, is described in which a gas stream is passed into thin walled tube 302 having a coating 310 of compound 60 on the inside of the tube as shown in FIGS. 10-11. The flow rate of the gas stream is controlled by valve 314. This is another example that allows for rapid heat-up using resistive heating system 320 while controlling the flow direction of the vaporized compound. After activating heating system 320 with actuator 330, current is passed along tube 302 in the heating/vaporization zone 340 as the carrier gas, e.g., air, N2 and the like, is passed through tube 302 and mixes with the resulting vapor. Another advantage of thin walled tube device 300 is that if drug is splattered from the interior wall of the tube before it can be vaporized, the drug will impact the other side of the hot tube where it would be vaporized. FIG. 12 shows an alternative heating system to resistive heating system 320 used in connection the third embodiment shown in FIGS. 10-11. In this case, inductive heating system 350 consists of a plurality of ferrites 360 for conducting the magnetic flux to vaporize drug 310.

Figure 13:
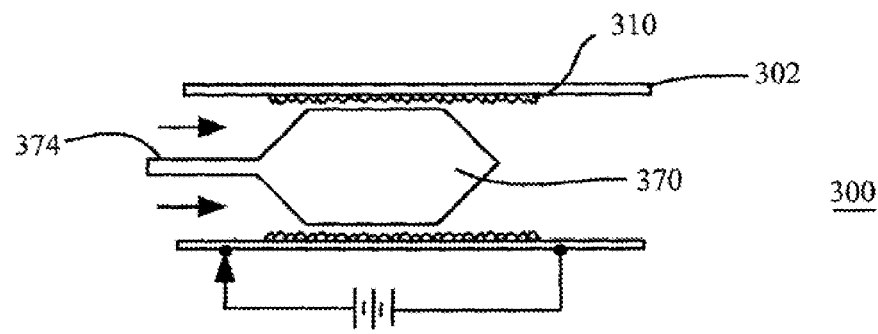
FIG. 13 is a schematic side view of an alternate embodiment of that shown in FIG. 10 using a flow restrictor within the thin-walled tube.

FIG. 13 shows the alternate to the third embodiment in which flow restrictor 370 is mounted within thin-walled tube 302 by means of support 374 within a housing (not shown) to increase the flow of mixing gas across the surface of a compound.

Example 4

In this example, device 400, the fourth embodiment of the present invention, is described. For this example, compound 60 is placed within expandable container 410, possibly a foil pouch, and is heated by resistance heater 420 upon being activated by actuator 430 as shown in FIG. 14. The vaporized compound generated is forced into container 410 through outlet passage 440 and mixed with the gas flowing through tube 450. While rapid heating will in some instances preclude or retard decomposition, additional steps may need to be taken to lower amount of decomposition to an acceptable level. One of these steps is to remove or reduce the presence of oxygen during the heat up period, is accomplished in this example by sealing the small container housing the compound with no atmosphere or in an inert-gas atmosphere.

Example 5

In this example, device 500, the fifth embodiment of the present invention is described in which the problem of the presence of oxygen during the heat-up period is also solved. Compound 60 is placed in an inert atmosphere or under a vacuum in container 502 within housing 10 and is heated by resistance heater 504 upon being activated by actuator 508 as shown in FIG. 15. Once compound 60 has become vaporized it can then be ejected through outlet passage 510 into the air stream passing through tube 520.

FIG. 16 shows an alternative to the embodiment shown in FIG. 15 in which fan 530 re-circulates the inert atmosphere over the surface of compound 60. The inert gas from a compressed gas cylinder (not shown) enters through inlet 540 and one-way valve 550 and exits through outlet passage 510 into tube 520 as in the above example.

Example 6

In this example, device 600, the sixth embodiment of the present invention is described in which compound 60 is deposited onto a substrate in the form of discrete particles 602, e.g., aluminum oxide (alumina), silica, coated silica, carbon, graphite, diatomaceous earth, and other packing materials commonly used in gas chromatography. The coated particles are placed within first tube 604 sandwiched between filters 604 and 608 and are heated by resistance heater 610 upon being activated by actuator 620 as shown in FIG. 17. The resulting vapor from tube 604 is combined with the air or other gas passing through second tube 625.

FIG. 18 shows an alternative to the embodiment shown in FIG. 17 in which resistance heater 630 heats the air prior to passing through first tube 604 and over discrete particles 602.

Example 7

If the decomposition of the compound is primarily caused by the presence of oxygen and not heat, and if the partial pressure of the compound is sufficient to produce the vaporization necessary at a temperature that does not produce decomposition, then an additional method of vaporization is possible. In device 700, the seventh embodiment of the present invention, compound 60 is deposited into chamber 710 and is heated by resistance heater 715 upon being activated by actuator 720 as shown in FIG. 19. Upon heating, some of compound 60 will vaporize and then become ejected from chamber 710 by moving an inert gas entering housing 10 through inert gas inlet 725 and valve 728 and passing across the surface of compound 60. The mixture of inert gas and vaporized compound passes through passage 730 and is then mixed with a gas passing through tube 735.

In Vitro Test Results for Example 7

A tank is partially filled with DOP and placed inside an oven (not shown) having an inlet and an outlet. DOP was used as the test compound. The tank was purged with helium prior to heating the tank and its contents to a temperature of 350° C. Helium was pumped through the tank and used to carry the DOP vapor out of the outlet. The gaseous mixture of helium and vaporized compound 60 was introduced into different size mixing tubes through a nozzle. Each of the tubes had air moving through them at 14 liters/minute. The nozzle was perpendicular to the flow direction. After this gaseous mixture was mixed with the air, the resulting aerosol was introduced into a parallel flow diffusion battery for particle size analysis. Results are set forth in Table 4 below.

TABLE 4

| Mixing tube size (ID) | MMAD | GSD |
| --- | --- | --- |
| 4.8 mm | 65 nm | 1.3 |
| 14 mm | 516 nm | 3.3 |

As can be seen above, as the tube diameter became larger so did the particle size. Additionally, as the diameter became larger, the GSD also became larger. As the tube becomes larger, it is believed that the vaporized gas is introduced into a smaller segment of the mixing gas because the gas is being introduced as a point source leading to uneven mixing, which results in a large GSD, as discussed under the DETAILED DESCRIPTION heading above.

Example 8

In this example, progressive heating is used during which multiple sections of a substrate are heated sequentially. The compound is deposited uniformly on the substrate. In order to subject the compound to rapid heat up, while at the same time not vaporizing the compound all at once, a movable heating zone is used. Compared to the entire surface area that the compound is laid down on, a relatively small heating area is generated in this example and moved, or "swept out" over the compound deposition area. A number of specific means for accomplishing this are described below.

1. Moving Heater Relative to Substrate

A variety of heating methods can be used to heat the substrate upon which a compound has been deposited. A small zone in the substrate can be heated or only a segment of the substrate or portion of the compound can be directly heated. In the preferred embodiment described in Example 1 above, an inductive heater heating method was utilized, which heated a zone in the foil substrate. Regardless of the heating method, as long as only a small zone of the compound and/or the substrate is heated, it is possible to move the heater relative to the substrate/compound. In the preferred embodiment, an inductive heating zone was induced in a conductive substrate that was in direct contact with the compound. The substrate was moved relative to this magnetic field, causing the compound to be locally vaporized.

2. Thermal Gradient

An alternative device for producing a moving heating zone was accomplished by device 800, the eighth embodiment of the present invention as shown in FIG. 20. Device 800 is referred as the gradient heating device. In device 800, thermally conductive substrate 802 was heated by resistance heater 810 at the upstream end of tube 820, and the thermal energy was allowed to travel along substrate 802. This produced, when observed in a particular location, a heat up rate that was determined from the characteristics of the thermally conductive substrate. By varying the material and its cross sectional area, it was possible to control the rate of heat up.

The source of the thermal energy can originate from a variety of other heating methods. A simple resistive heater 810 is shown. This resistive heater was embedded in substrate 802 at one end. However, it could be embedded into both ends, or in a variety of positions along the substrate and still allow the temperature gradient to move along the carrier and/or substrate shown in FIG. 20.

To demonstrate effectiveness of a thermal gradient device, a 4-inch long piece of aluminum was fitted with a 150-watt cartridge heater at one end. The heater was powered with a variac AC power transformer. The thickness of the aluminum was designed to ensure that heat would transverse from one end of the aluminum to the other in approximately 30 seconds.

On the topside of the aluminum, an indentation was machined to hold the compound and to hold one of two top covers. The indentation for the compound was approximately 3.5 inches long and 0.4 inches wide. The indentation was 0.025 inches deep, and was filled with 1 mg of DOP.

The first top consisted of a sheet of flat glass placed 0.04 inches above the heated surface, creating an airway. At the exit end an outlet was fitted allowing the air to be drawn into an analytical measurement device. Air was made to flow through the airway at a rate of 15 liters/minute.

In the second configuration, the top was replaced with a half cylinder made of glass. This increased the cross sectional area of the airway by an order of magnitude.

Particle size was measured with both configurations and shown to be affected by the cross sectional area of the airway.

Results from the thermal gradient test are set forth in Table 5 below:

TABLE 5

| Cover size and cross-section | MMAD | GSD |
| --- | --- | --- |
| Small | 92 nm | 1.4 |
| Big | 650 nm | unknown |

As shown above, the results confirm that as the cross section becomes larger, so does the particle size.

3. Discrete Heating Zones

A third method established a set of heated zones, energized sequentially. The zones could be produced from any of the heating devices including a resistive heater as disclosed in Rosen, PCT Publication No. 94/09842, published May 11, 1994, the relevant portions of which are incorporated herein by reference. For example, a substrate could have three (3) sections A, B, C where section A is first heated until the compound have been vaporized followed by the section B, and then C.

4. Inductive Heater, Vary Field to Heat Different Zones

A fourth method involved heating a zone in a substrate with an inductive heater, and then by manipulating the magnetic field, causing the induced current in the substrate to move along the substrate. This was accomplished by a number of methods. One method was to use a ferrite with a saturation value such that, by increasing the electrical field internal to the ferrite, the resultant magnetic field leaves the confines of the ferrite and enters a different area of the substrate.

Another method involved constructing a ferrite with a shape that can be changed, such as opening up an air gap, and thereby changing the shape of the magnetic field.

5. The Use of Radiative Heating

An additional method involved incrementally heating a substrate through the focusing and/or de-focusing of all forms of photon energy, especially in the visible and IR spectrum.

Example 9

The ninth embodiment of the present invention is shown in FIGS. 21-22 as screen device 900. In device 900, air was channeled through a fine mesh metal screen 902 that had the drug deposited thereon. Rapid heating and/or rapid cooling, as stated above, can preclude decomposition. This example involves rapidly mixing a compound, once it has vaporized, into air. A thin (0.01 to 10 micron) layer of compound can be deposited onto fine mesh screen 902, e.g., 200 and 400 mesh screens were used in this example. Screen 902 was positioned across airway passage 910. In this preferred embodiment for producing fine aerosols, airway passage 910 was constructed from 18 mm diameter glass tubing. However, the passage can be made in any shape with a comparable cross-sectional area and out of any suitable material. The screen size, mesh, and the amount of compound were chosen in this example so that a gas could pass through the screen without interference once the compound had been deposited on it.

The two sides of the screen were electrically connected to charged capacitor 920 through silicon-controlled rectifier (SCR) 922 to make a circuit. The charge of the capacitor was calculated and set at a value such that, when actuator 930 closed SCR 922, the energy from capacitor 920 was converted to a desired temperature rise in screen 902. Because the internal resistance of the screen was low, i.e., between 0.01 and 0.2 ohms, the discharge rate (the RC time constant) of the capacitor was rapid, and on the order of a few milliseconds, i.e. less than 20 milliseconds, preferably in the range of about 2 to about 10 milliseconds. Upon discharge of capacitor 902 and the subsequent heating of screen 902, the deposited compound was rapidly vaporized. Because air moved through screen 902, the vaporized compound rapidly mixed with air and cooled.

The compound was deposited onto the fine stainless steel screen, e.g., 200 mesh, made from 316 stainless steel, having measurements of 2.54 cm.×2.54 cm. The current from the capacitor was passed between one edge and another. It was not necessary to heat the screen to temperatures comparable to the thin foil in Example 1, because the compound vaporized at a lower temperature due to the rapid air movement. Rapid air movement allowed the compound to vaporize at a lower vapor pressure, since airflow constantly removed compound vapors from the surface as soon as they were formed. Thus, the compound vaporized at a lower temperature without decomposition.

Deposition of the compound onto the screen was accomplished by mixing the compound with an organic solvent until the compound dissolved. The resulting solution was then applied to the fine stainless steel screen 902 and the solvent was allowed to evaporate. The screen was then inserted into holder 940 that electrically connected two sides of screen 902 to the power circuit described above.

A 10,000 mF capacitor was discharged while the gas was passing through screen 902. The rapid heat up of the screen resulted in a rapid vaporization of the compound into the gas. Thus the resulting vaporized compound was mixed into a small volume of the gas. Because the ratio of the mass of the compound to the volume of the mixing gas was large, a fine (1-3 micron diameter) particle aerosol was made.

One of ordinary skill in the art can combine the foregoing embodiments or make various other embodiments and aspects of the method and device of the present invention to adapt them to specific usages and conditions. As such, these changes and modifications are properly, equitably, and intended to be, within the full range of equivalents of the following claims.

What is claimed is:

1. A method for generating an aerosol comprising the steps of:
   (a) depositing a coating comprising a physiologically active compound onto a substrate comprising dissolving the compound in an organic solvent, applying the solution to all or a portion of the substrate and allowing the solvent to evaporate;
   (b) heating the physiologically active compound to vaporize at least a portion of the compound, following said evaporation;
   (c) cooling the resulting vapor by mixing the vapor with a gas in a predetermined ratio, selected to form an aerosol comprised of particles within a desired size range when a stable concentration of particles in the gas is reached.

2. The method of claim 1 wherein the desired size range is a mass median aerodynamic diameter between about 1 to 3 microns.

3. The method of claim 1 wherein the desired size range is a mass median aerodynamic diameter between about 10 to 100 nanometers.

4. The method of claim 1 wherein the gas is air.

5. The method of claim 1 wherein the compound is selected from the group consisting of cannabinoid extracts from cannabis, THC, ketorolac, fentanyl, morphine, testosterone, ibuprofen, codeine, nicotine, Vitamin A, Vitamin E acetate, Vitamin E, nitroglycerin, pilocarpine, mescaline, testosterone enanthate, menthol, phencaramide, methsuximide, eptastigmine, promethazine, procaine, retinol, lidocaine, trimeprazine, isosorbide dinitrate, timolol, methyprylon, etamiphyllin, propoxyphene, salmetrol, vitamin E succinate, methadone, oxprenolol, isoproterenol bitartrate, etaqualone, Vitamin D3, ethambutol, ritodrine, omoconazole, cocaine, lomustine, ketamine, ketoprofen, cilazaprol, propranolol, sufentanil, metaproterenol, pentoxapylline, captopril, loxapine, cyproheptidine, carvediol, trihexylphenadine, alprostadil, melatonin, testosterone proprionate, valproic acid, acebutolol, terbutaline, diazepam, topiramate, pentobarbital, alfentanil HCl, papaverine, nicergoline, fluconazole, zafirlukast, testosterone acetate, droperidol, atenolol, metoclopramide, enalapril, albuterol, ketotifen, isoproterenol, amidarone HCl, zileuton, midazolam, oxycodone, cilostazol, propofol, nabilone, gabapentin, famotidine, lorezepam, naltrexone, acetaminophen, sumatriptan, bitolterol, nifedipine, phenobarbital, phentolamine, 13-cis retinoic acid, dropenilamine HCl, amlodipine, caffeine, zopiclone, tramadol HCl, pirbuterol, naloxone, meperidine HCl, trimethobenzamide, nalmefene, scopolamine, sildenafil, carbamazepine, procaterol HCl, methysergide, glutathione, olanzapine, zolpidem, levorphanol, buspirone and mixtures thereof.

6. The method of claim 1 wherein an inhalation dose of the compound is vaporized over a period of time no greater than 2 seconds.

7. The method of claim 1 wherein the mixing comprises passing the gas across the surface of the coating.

8. The method of claim 1 further comprising administering the resulting aerosol to a patient.

9. The method of claim 1 wherein the stable concentration is about $10^9$ particles/cc.

10. A method for generating an aerosol comprising the steps of:
(a) depositing a coating comprising a physiologically active compound onto a substrate comprising dissolving the compound in an organic solvent, applying the solution to all or a portion of the substrate and allowing the solvent to evaporate;
(b) heating a coating comprising a therapeutic amount of said physiologically active compound deposited onto said substrate to vaporize at least a portion of the compound, following said evaporation;
(c) cooling the resulting vapor by mixing the vapor with a gas in a predetermined ratio, selected to form an aerosol comprised of particles within a desired size range when a stable concentration of particles in the gas is reached.

11. The method of claim 10 wherein the desired size range is a mass median aerodynamic diameter between about 1 to 3 microns.

12. The method of claim 10 wherein the desired size range is a mass median aerodynamic diameter between about 10 to 100 nanometers.

13. The method of claim 10 wherein the gas is air.

14. The method of claim 10 wherein an inhalation dose of the compound is vaporized over a period of time no greater than 2 seconds.

15. The method of claim 10 wherein the mixing comprises passing the gas across the surface of the coating.

16. The method of claim 10 further comprising administering the resulting aerosol to a patient.

17. The method of claim 10 wherein the stable concentration is about $10^9$ particles/cc.

18. A method for generating an aerosol comprising the steps of:
(a) depositing a coating comprising a physiologically active compound onto a substrate comprising dissolving the compound in an organic solvent, applying the solution to all or a portion of the substrate and allowing the solvent to evaporate
(b) heating the physiologically active compound to vaporize at least a portion of the compound, following said evaporation;
(c) cooling the resulting vapor by mixing the vapor with a gas in a predetermined ratio, selected to form an aerosol comprised of particles within a desired size range that are sufficiently stable that they will remain within that range during the time necessary to administer the aerosol to a patient.

19. The method of claim 18 wherein the desired size range is a mass median aerodynamic diameter between about 1 to 3 microns.

20. The method of claim 18 wherein the desired size range is a mass median aerodynamic diameter between about 10 to 100 nanometers.

21. The method of claim 18 wherein the gas is air.

22. The method of claim 18 wherein the compound is selected from the group consisting of cannabinoid extracts from cannabis, THC, ketorolac, fentanyl, morphine, testosterone, ibuprofen, codeine, nicotine, Vitamin A, Vitamin E acetate, Vitamin E, nitroglycerin, pilocarpine, mescaline, testosterone enanthate, menthol, phencaramide, methsuximide, eptastigmine, promethazine, procaine, retinol, lidocaine, trimeprazine, isosorbide dinitrate, timolol, methyprylon, etamiphyllin, propoxyphene, salmetrol, vitamin E succinate, methadone, oxprenolol, isoproterenol bitartrate, etaqualone, Vitamin D3, ethambutol, ritodrine, omoconazole, cocaine, lomustine, ketamine, ketoprofen, cilazaprol, propranolol, sufentanil, metaproterenol, pentoxapylline, captopril, loxapine, cyproheptidine, carvediol, trihexylphenadine, alprostadil, melatonin, testosterone proprionate, valproic acid, acebutolol, terbutaline, diazepam, topiramate, pentobarbital, alfentanil HCl, papaverine, nicergoline, fluconazole, zafirlukast, testosterone acetate, droperidol, atenolol, metoclopramide, enalapril, albuterol, ketotifen, isoproterenol, amidarone HCl, zileuton, midazolam, oxycodone, cilostazol, propofol, nabilone, gabapentin, famotidine, lorezepam, naltrexone, acetaminophen, sumatriptan, bitolterol, nifedipine, phenobarbital, phentolamine, 13-cis retinoic acid, dropenilamine HCl, amlodipine, caffeine, zopiclone, tramadol HCl, pirbuterol, naloxone, meperidine HCl, trimethobenzamide, nalmefene, scopolamine, sildenafil, carbamazepine, procaterol HCl, methysergide, glutathione, olanzapine, zolpidem, levorphanol, buspirone and mixtures thereof.

23. The method of claim 18 wherein an inhalation dose of the compound is vaporized over a period of time no greater than 2 seconds.

24. The method of claim 18 wherein the mixing comprises passing the gas across the surface of the coating.

25. The method of claim 18 further comprising administering the resulting aerosol to a patient.

26. A method for generating an aerosol comprising the steps of:

(a) depositing a coating comprising a compound onto a substrate comprising dissolving the compound in an organic solvent, applying the solution to all or a portion of the substrate and allowing the solvent to evaporate;
(b) heating a coating comprising a therapeutic amount of a physiologically active compound deposited onto said substrate to vaporize at least a portion of the compound, following said evaporation;
(c) cooling the resulting vapor by mixing the vapor with a gas in a predetermined ratio, selected to form an aerosol comprised of particles within a desired size range that are sufficiently stable that they will remain within that range during the time necessary to administer the aerosol to a patient.

27. The method of claim 26 wherein the particle size is a mass median aerodynamic diameter between about 1 to 3 microns.

28. The method of claim 26 wherein the particle size is a mass median aerodynamic diameter between about 10 to 100 nanometers.

29. The method of claim 26 wherein the gas is air.

30. The method of claim 26 wherein an inhalation dose of the compound is vaporized over a period of time no greater than 2 seconds.

31. The method of claim 26 wherein the mixing comprises passing the gas across the surface of the coating.

32. The method of claim 26 further comprising administering the resulting aerosol to a patient.

* * * * *